(12) United States Patent
Stickney et al.

(10) Patent No.: US 8,160,703 B2
(45) Date of Patent: Apr. 17, 2012

(54) APPARATUS, SOFTWARE, AND METHODS FOR CARDIAC PULSE DETECTION USING A PIEZOELECTRIC SENSOR

(75) Inventors: Ronald E. Stickney, Edmonds, WA (US); Cynthia P. Jayne, Redmond, WA (US); Paula Lank, Newcastle, WA (US); Patricia O'Hearn, Mercer Island, WA (US); Tae H. Joo, Redmond, WA (US); David R. Hampton, Woodinville, WA (US); Richard C. Nova, Kirkland, WA (US); Patrick F. Kelly, Edmonds, WA (US); William E. Saltzstein, Woodinville, WA (US)

(73) Assignee: Physio-Control, Inc., Redmond, WA (US)

( * ) Notice: Subject to any disclaimer, the term of this patent is extended or adjusted under 35 U.S.C. 154(b) by 1718 days.

(21) Appl. No.: 11/187,616

(22) Filed: Jul. 22, 2005

(65) Prior Publication Data
US 2006/0167515 A1    Jul. 27, 2006

Related U.S. Application Data

(63) Continuation-in-part of application No. 10/229,321, filed on Aug. 26, 2002, now abandoned, and a continuation-in-part of application No. 10/229,320, filed on Aug. 26, 2002, which is a continuation-in-part of application No. 09/410,198, filed on Sep. 30, 1999, now Pat. No. 6,440,082, and a continuation-in-part of application No. 10/013,941, filed on Dec. 6, 2001, now abandoned.

(51) Int. Cl.
*A61N 1/362* (2006.01)
(52) U.S. Cl. .......................................... 607/19
(58) Field of Classification Search .................. 607/4, 5, 607/6, 7, 8, 9, 10, 11, 12, 13, 14, 15, 16, 607/17
See application file for complete search history.

(56) References Cited

U.S. PATENT DOCUMENTS 3,716,059 A    2/1973    Welborn et al.
(Continued)

FOREIGN PATENT DOCUMENTS

EP    0 339 471 A2    11/1989
(Continued)

OTHER PUBLICATIONS

Akira, I., et al., "Pattern Classification of the Phonocardiogram Using Linear Prediction Analysis ," *Medical & Biological Engineering & Computing* 15(4):407-412, Jul. 1977.

(Continued)

*Primary Examiner* — Carl H Layno
*Assistant Examiner* — Roland Dinga
(74) *Attorney, Agent, or Firm* — Marger Johnson & McCollom

(57) ABSTRACT

Signal data obtained from a piezoelectric sensor placed on a patient's body is used to detect the presence of a cardiac pulse. The piezoelectric sensor has a transducing element adapted to sense movement due to a cardiac pulse and produce piezoelectric signal data in response thereto. Processing circuitry analyzes the piezoelectric signal data for a feature indicative of a cardiac pulse and determines whether a cardiac pulse is present in the patient based on the feature. In one aspect, the feature may be a temporal feature such as a relative change in energy. In another aspect, the feature may be a spectral feature such as the energy or frequency of a peak in the energy spectrum of the signal. In yet another aspect, the feature may be obtained by comparing the piezoelectric signal data with a previously-identified pattern known to predict the presence of a cardiac pulse. Multiple features may also be obtained from the piezoelectric signal data and classified to determine the presence of a cardiac pulse.

3 Claims, 16 Drawing Sheets

U.S. PATENT DOCUMENTS

| | | | |
|---|---|---|---|
| 3,871,359 A | 3/1975 | Pacela | |
| RE30,101 E | 9/1979 | Kubicek et al. | |
| 4,181,134 A | 1/1980 | Mason et al. | |
| 4,220,160 A | 9/1980 | Kimball et al. | |
| RE30,750 E | 9/1981 | Diack et al. | |
| 4,291,699 A | 9/1981 | Geddes et al. | |
| 4,428,380 A | 1/1984 | Wong et al. | |
| 4,446,873 A | 5/1984 | Groch et al. | |
| 4,450,527 A | 5/1984 | Sramek | |
| 4,519,397 A | 5/1985 | Tabata | |
| 4,548,204 A | 10/1985 | Groch et al. | |
| 4,559,946 A | 12/1985 | Mower | |
| 4,562,843 A | 1/1986 | Djordjevich et al. | |
| 4,610,254 A | 9/1986 | Morgan et al. | |
| 4,777,962 A | 10/1988 | Watson et al. | |
| 4,792,145 A | 12/1988 | Eisenberg et al. | |
| 4,896,675 A | 1/1990 | Ohsuga et al. | |
| 4,919,145 A | 4/1990 | Marriott | |
| 4,928,690 A * | 5/1990 | Heilman et al. | 607/4 |
| 4,947,859 A * | 8/1990 | Brewer et al. | 600/528 |
| 4,951,679 A | 8/1990 | Harada | |
| 4,967,760 A | 11/1990 | Bennett, Jr. et al. | |
| 5,002,052 A | 3/1991 | Haluska | |
| 5,035,247 A | 7/1991 | Heimann | |
| 5,036,857 A | 8/1991 | Semmlow et al. | |
| 5,077,667 A | 12/1991 | Brown et al. | |
| 5,078,134 A | 1/1992 | Heilman et al. | |
| 5,178,154 A | 1/1993 | Ackmann et al. | |
| 5,243,975 A | 9/1993 | Alferness et al. | |
| 5,261,418 A * | 11/1993 | Ferek-Petric | 607/126 |
| 5,273,036 A | 12/1993 | Kronberg et al. | |
| 5,305,745 A | 4/1994 | Zacouto | |
| 5,318,592 A | 6/1994 | Schaldach | |
| 5,337,752 A | 8/1994 | Reeves | |
| 5,339,819 A | 8/1994 | Takashima | |
| 5,353,793 A | 10/1994 | Bornn | |
| 5,362,966 A | 11/1994 | Rosenthal et al. | |
| 5,366,486 A | 11/1994 | Zipes et al. | |
| 5,392,780 A | 2/1995 | Ogino et al. | |
| 5,404,877 A | 4/1995 | Nolan et al. | |
| 5,405,362 A * | 4/1995 | Kramer et al. | 607/5 |
| 5,423,326 A | 6/1995 | Wang et al. | |
| 5,425,750 A | 6/1995 | Moberg | |
| 5,431,688 A * | 7/1995 | Freeman | 607/10 |
| 5,433,731 A | 7/1995 | Hoegnelid et al. | |
| 5,443,072 A | 8/1995 | Kagan et al. | |
| 5,458,621 A | 10/1995 | White et al. | |
| 5,474,574 A * | 12/1995 | Payne et al. | 607/7 |
| 5,490,516 A | 2/1996 | Hutson | |
| 5,497,779 A | 3/1996 | Takaya et al. | |
| 5,617,868 A | 4/1997 | Harada et al. | |
| 5,620,003 A | 4/1997 | Sepponen | |
| 5,622,182 A | 4/1997 | Jaffe | |
| 5,683,424 A | 11/1997 | Brown et al. | |
| 5,685,317 A | 11/1997 | Sjostrom | |
| 5,687,738 A | 11/1997 | Shapiro et al. | |
| 5,700,283 A | 12/1997 | Salo | |
| 5,702,427 A | 12/1997 | Ecker et al. | |
| 5,704,363 A | 1/1998 | Amano | |
| 5,727,561 A | 3/1998 | Owsley | |
| 5,776,071 A | 7/1998 | Inukai et al. | |
| 5,795,300 A * | 8/1998 | Bryars | 600/500 |
| 5,807,268 A | 9/1998 | Reeves et al. | |
| 5,825,895 A | 10/1998 | Grasfield et al. | |
| 5,885,222 A | 3/1999 | Kassal et al. | |
| 6,005,658 A | 12/1999 | Kaluza et al. | |
| 6,050,950 A | 4/2000 | Mohler | |
| 6,053,872 A | 4/2000 | Mohler | |
| 6,104,953 A * | 8/2000 | Leyde | 607/4 |
| 6,122,536 A | 9/2000 | Sun et al. | |
| 6,125,298 A | 9/2000 | Olson et al. | |
| 6,125,299 A | 9/2000 | Groenke et al. | |
| 6,141,584 A | 10/2000 | Rockwell et al. | |
| 6,155,257 A | 12/2000 | Lurie et al. | |
| 6,161,038 A | 12/2000 | Schookin et al. | |
| 6,171,256 B1 | 1/2001 | Joo et al. | |
| 6,179,783 B1 | 1/2001 | Mohler | |
| 6,293,915 B1 | 9/2001 | Amano et al. | |
| 6,298,267 B1 | 10/2001 | Rosborough et al. | |
| 6,304,773 B1 * | 10/2001 | Taylor et al. | 600/515 |
| 6,304,780 B1 | 10/2001 | Owen et al. | |
| 6,312,399 B1 | 11/2001 | Lurie et al. | |
| 6,356,785 B1 | 3/2002 | Snyder et al. | |
| 6,371,920 B1 | 4/2002 | Kamimoto et al. | |
| 6,428,483 B1 | 8/2002 | Carlebach | |
| 6,440,082 B1 * | 8/2002 | Joo et al. | 600/528 |
| 6,443,906 B1 | 9/2002 | Ting et al. | |
| 6,501,983 B1 | 12/2002 | Natarajan et al. | |
| 6,575,914 B2 * | 6/2003 | Rock et al. | 600/500 |
| 6,587,723 B1 * | 7/2003 | Sloman et al. | 607/28 |
| 6,650,940 B1 | 11/2003 | Zhu et al. | |
| 2001/0039383 A1 | 11/2001 | Mohler | |
| 2001/0047140 A1 | 11/2001 | Freeman | |
| 2002/0032383 A1 | 3/2002 | Weil et al. | |
| 2002/0072685 A1 | 6/2002 | Rymut et al. | |
| 2002/0165585 A1 * | 11/2002 | Dupelle et al. | 607/5 |
| 2002/0173725 A1 | 11/2002 | Rock et al. | |
| 2003/0060723 A1 | 3/2003 | Joo et al. | |
| 2003/0109790 A1 | 6/2003 | Stickney et al. | |
| 2004/0039419 A1 | 2/2004 | Stickney et al. | |
| 2004/0039420 A1 | 2/2004 | Jayne et al. | |
| 2005/0240234 A1 | 10/2005 | Joo et al. | |
| 2010/0114219 A1 | 5/2010 | Stickney et al. | |
| 2010/0121208 A1 | 5/2010 | Stickney et al. | |
| 2010/0121392 A1 | 5/2010 | Stickney et al. | |

FOREIGN PATENT DOCUMENTS

| | | |
|---|---|---|
| EP | 0 435 500 A1 | 7/1991 |
| EP | 1 057 498 A2 | 12/2000 |
| GB | 2 150 332 | 6/1985 |
| WO | WO 84/01705 | 5/1984 |
| WO | WO 93/22970 | 11/1993 |
| WO | WO 97/05821 | 2/1997 |
| WO | 0122885 A1 | 4/2001 |

OTHER PUBLICATIONS

Alt, E., et al., "Feasibility of Using Intracardiac Impedance Measurements for Capture Detection," *Pacing and Clinical Electrophysiology* 15:1873-1879, Nov., Part II, 1992.

"American Heart Guidelines 2000 for Cardiopulmonary Resuscitation and Emergency Cardiovasular Care, Part 3: Adult Basic Life Support," *Circulation* 102 Suppl. I:I-22 to I-59, 2000.

Bahr, J., "Skills of Lay People in Checking the Carotid Pulse," *Resuscitation* 35:23-26, 1997.

Bogaard, H.J., et al., "Assessment of the Haemodynamic Response to Exercise by Means of Electrical Impedance Cardiography: Method, Validation and Clinical Applications," *Physiological Measurement* 18:95-105, May 1997.

Bulgrin, J.R., et al., "Comparison of Short-time Fourier, Wavelet and Time-domain Analyses of Intracardiac Sounds" *Biomedical Sciences Instrumentation* 29:465-472, 1993, ISA Paper #93-059.

CardioDynamics, "What Is the BioZ® ICG Test?" http://www.cardiodynamics.com/cdpati10.html [accessed Dec. 8, 2005.].

CardioDynamics, BioZ Technology, "ICG Technology," <http://www.cardiodynamics.com/cdprod40.html> [accessed Dec. 2005.].

L. Cobb et al., "Influence of Cardiopulmonary Resuscitation Prior to Defibrillation in Patients With Out-of-Hospital Ventricular Fibrillation," *JAMA* 281:1182-1188 (1999).

R. Duda and P. Hart, "Pattern Classification and Scene Analysis," published by John Wiley & Sons, New York, pp. 1-482, (1973).

Eberle, B., et al., "Checking the Carotid Pulse Check: Diagnostic Accuracy of First Responders in Patients With and Without a Pulse," *Resuscitation* 33:107-116, 1996.

Geddes, L.A., and L.E. Baker, *Doppler: Principals of Applied Biomedical Instrumentation*, 3d ed., John Wiley and Sons, New York, 1989, "Applications of Ultrasound," pp. 184-209.

Gravenstein, J.S., et al., *$CO_2$: Gas Monitoring in Clinical Practice*, 2d ed., Butterworth-Heinemann, Boston, 1995, Chap. 4, "Monitoring Carbon Dioxide," pp. 23-42.

Gulcur et al., "Estimation of Systolic Blood Pressure from the Second Heart Sounds," $2^{nd}$ *International Biomedical Engineering Days*, 1998, pp. 39-40.

Hasegawa, M.D., and S. Rodbard, M.D., Ph.D., "Delayed Timing of Heart and Arterial Sounds in Patients with Implanted Pacemakers," *Journal of Thoracic and Cardiovascular Surgery* 72(1):62-66, Jul. 1976.

Hoffman, S., et al., "Respiratory Monitoring With a New Impedance Plethysmograph," *Anaesthesia* 41:1139-1142, 1986.

Hu, W., et al., "A Study on Methods for Impedance Cardiography," *Proceedings—19th International Conference—IEEE/EMBS*, Chicago, Oct. 30-Nov. 2, 1997, pp. 2074-2077.

Johnston, P.W., et al., "The Transthoracic Impedance Cardiogram Is a Potential Haemodynamic Sensor for an Automated External Defibrillator," *European Heart Journal* 19:1879-1888, Dec. 1998.

Kassal, J. et al., "Polymer-Based Adherent Differential-Output Sensor for Cardiac Auscultation," *Medical Electronics*, Sep. 1994, pp. 54-63.

S.M. Kay, "Modern Spectral Estimation: Theory and Application," published by Prentice Hall of Englewood Cliffs, New Jersey pp. 182-183 (1988).

"±5 g to ±50 g, Low Noise, Low Power, Single/Dual Axis iMEMS® Accelerometers (ADXL150/ADXL250—Specifications)," Analog Devices, Inc., Rev. 0, 1998.

Kubicek, W.G., et al., "Development and Evaluation of an Impedance Cardiac Output System," *Aerospace Medicine* 37:1208-1212, Dec. 1966.

Lehner, R.J.; Rangayyan, R.M., "Microcomputer System for Quantification of the Phonocardiogram," *Proceedings of the Seventh Annual Conference of the IEEE/Engineering in Medicine and Biology Society* 2(2):849-854, 1986.

Luisada, A.A., "The First Heart Sound in Normal and Pathological Conditions," *Japanese Heart Journal*, 28(2):143-156, Mar. 1987.

Measurement Specialities, Inc., "Piezo Film Sensors Technical Manual," Internet Version, Aug. 1998.

Mehlsen, J., et al., "A Comparison of Systolic Time Intervals Measured by Impedance Cardiography and Carotid Pulse Tracing," *Danish Medical Bulletin* 37(1):93-95, Feb. 1990.

Muzi, M., et al., "Clinical Application of ECG R-Wave Triggered, Ensemble-Averaged Impedance Waveforms," *Annual Interntational Conference of the IEEE Engineering in Medicine and Biology Society* 12(5):1991, 1990.

Ochoa et al., "Competence of Health Professionals to Check the Carotid Pulse," *Resuscitation* 37:173-175, 1998.

Rosell, J., and J.G. Webster, "Signal-to-Motion Artifact Ratio Versus Frequency for Impedance Pneumography," *IEEE Transactions on Biomedical Engineering* 42(3):321-323, Mar. 1995.

Stodieck, L.S., and M.W. Luttges, "Relationships Between the Electrocardiogram and Phonocardiogram: Potential for Improved Heart Monitoring," *ISA Transactions*, 23(4):59-65, Apr. 1984.

Wang, X., et al., "Impedance Cardiac Profile Monitoring by a Modified Ensemble Averaging Technique," *Proceeds of the IEEE Engineering in Medicine and Biology Society 10th Annual International Conference* 1:39-40, New Orleans, 1988.

Watanabe, K., et al., "Computer Analysis of the Exercise ECG: A Review," *Progress in Cardiovascular Diseases* XXII(6):423-446, May/Jun. 1980.

Woltjer, H.H., et al., "The Technique of Impedance Cardiography," *European Heart Journal* 18:1396-1403, Sep. 1997.

Office Action dated Dec. 29, 2009, from U.S. Appl. No. 11/167,247, pp. 5.

Response to Office Action dated Dec. 29, 2009, from U.S. Appl. No. 11/167,247, filed Mar. 26, 2010, pp. 15.

Office Action from U.S. Appl. No. 11/167,247, dated Oct. 1, 2008, 12 pp.

Response to Office Action dated Oct. 1, 2008, from U.S. Appl. No. 11/167,247, filed Feb. 2, 2009, 16 pp.

Office Action from U.S. Appl. No. 11/167,247, dated Apr. 30, 2009, 6 pp.

Response to Office Action dated Apr. 30, 2009, from U.S. Appl. No. 11/167,247, filed Jul. 30, 2009, 19 pp.

Advisory Action from U.S. Appl. No. 11/167,247, dated Aug. 14, 2009, 3, pp.

Response to Advisory Action dated Aug. 14, 2009, from U.S. Appl. No. 11/167,247, filed filed Sep. 30, 2009, 20 pp.

Office Action from U.S. Appl. No. 11/167,247, dated Jun. 28, 2010, 5 pp.

Restriction Requirement from U.S. Appl. No. 11/737,703, dated Dec. 2, 2009, 6 pp.

Response to Restriction Requirement dated Dec. 2, 2009, from U.S. Appl. No. 11/737,703, filed Dec. 30, 2009, 5 pp.

Restriction Requirement from U.S. Appl. No. 10/229,339, dated Sep. 6, 2005, 6 pp.

Response to Restriction Requirement dated Sep. 6, 2005, from U.S. Appl. No. 10/229,339, filed Oct. 6, 2005, 3 pp.

Office Action from U.S. Appl. No. 10/229,339, dated Dec. 27, 2005, 12 pp.

Response to Office Action dated Dec. 27, 2005, from U.S. Appl. No. 10/229,339, filed Jun. 5, 2006, 30 pp.

Office Action from U.S. Appl. No. 10/229,339, dated Oct. 12, 2006, 9 pp.

Office Action from U.S. Appl. No. 11/737,703, dated Nov. 1, 2010, 7 pp.

Response to Office Action dated Nov. 1, 2010, from U.S. Appl. No. 11/737,703, filed Jan. 31, 2011, 6 pp.

Geddes et al., "Cyclops Whistler—A Noninvasive Audible Monitor for the Amplitude of the Arterial Pulse," Cardiovascular Engineering, vol. 5, No. 2, 97-102, 2005.

Farag et al., "Detection of pulse and respiratory signals from the wrist using dry electrodes," Biomedical instrumentation technology Association for the Advancement of Medical Instrumentation, Jul./Aug. 1994, 5 pp.

Renevey et al., "Wrist-located pulse detection using IR signals, activity and nonlinear artifact cancellation," 2001 Conference Proceedings of the 23rd Annual International Conference of the IEEE Engineering in Medicine and Biology Society, Istanbul, Turkey, Oct. 25-28, 2001, 4 pp.

Tibballs et al., "Reliability of pulse palpation by health care personnel to diagnose pediatric cardiac arrest," Resuscitation, 2009;80:61-64.

Lapostolle et al., "Basic cardiac life support providers checking the carotid pulse: performance, degree of conviction, and influencing factors," Acad Emerg Med. 2004; 11:878-880.

Kubicek, Development and Evaluation of an Impedance Cardiographic System to Measure Cardiac Output and Other Cardiac Parameters, National Aeronautics and Space Administration (NASA), Jul. 1, 1968 to Jun. 30, 1969, 472 pp.

Kubicek et al., "Impedance Cardiography As a Noninvasive Method of Monitoring Cardiac Function and Other Parameters of the Cardiovascular System," Annals of the New York Academy of Sciences 170, No. 2 (Jul. 1, 1970): 724-732.

* cited by examiner

APPARATUS, SOFTWARE, AND METHODS FOR CARDIAC PULSE DETECTION USING A PIEZOELECTRIC SENSOR

This application is a continuation-in-part of U.S. patent application Ser. No. 10/229,321, filed Aug. 26, 2002. This application is also a continuation-in-part of U.S. patent application Ser. No. 10/229,320, filed Aug. 26, 2002, which is a continuation-in-part of U.S. patent application Ser. No. 09/410,198, filed Sep. 30, 1999, now issued as U.S. Pat. No. 6,440,082, and U.S. patent application Ser. No. 10/013,941, filed Dec. 6, 2001. The entire content of all the applications is incorporated herein by reference.

FIELD OF THE INVENTION

The present invention relates to detection of cardiac activity in a patient, and more specifically, to detection of a cardiac pulse and use of pulse detection in delivering therapy.

BACKGROUND OF THE INVENTION

The presence of a cardiac pulse in a patient is typically detected by palpating the patient's neck and sensing changes in the volume of the patient's carotid artery due to blood pumped from the patient's heart. When the heart's ventricles contract during a heartbeat, a pressure wave is sent throughout the patient's peripheral circulation system. A carotid pulse waveform rises with the ventricular ejection of blood at systole and peaks when the pressure wave from the heart reaches a maximum. The carotid pulse falls off again as the pressure subsides toward the end of the pulse.

The absence of a detectable cardiac pulse in a patient is a strong indicator of cardiac arrest. Cardiac arrest is a life-threatening medical condition in which the patient's heart fails to provide sufficient blood flow to support life. During cardiac arrest, the electrical activity of the heart may be disorganized (ventricular fibrillation), too rapid (ventricular tachycardia), absent (asystole), or organized at a normal or slow heart rate without producing sufficient blood flow (pulseless electrical activity).

The form of therapy to be provided to a patient in cardiac arrest depends, in part, on an assessment of the patient's cardiac condition. For example, a caregiver may apply a defibrillation shock to a patient experiencing ventricular fibrillation (VF) or ventricular tachycardia (VT) to stop the unsynchronized or rapid electrical activity and allow a perfusing rhythm to return. External defibrillation, in particular, is provided by applying a strong electric pulse to the patient's heart through electrodes placed on the surface of the patient's body. If the patient lacks a detectable pulse and is experiencing asystole or pulseless electrical activity (PEA), a caregiver may perform cardiopulmonary resuscitation (CPR), which causes some blood to flow in the patient.

Before providing therapy such as defibrillation or CPR to a patient, a caregiver must first confirm that the patient is in cardiac arrest. In general, external defibrillation is suitable only for patients that are unconscious, apneic, pulseless, and in VF or VT. Medical guidelines indicate that the presence or absence of a cardiac pulse in a patient should be determined within 10 seconds. See "American Heart Guidelines 2000 For Cardiopulmonary Resuscitation and Emergency Cardiovascular Care, Part 3: Adult Basic Life Support," *Circulation* 102 Suppl. I:I-22 to I-59, 2000.

Unfortunately, under the pressure and stress of an emergency situation, it can be extremely difficult for first-responding caregivers with little or no medical training to consistently and accurately detect a cardiac pulse in a patient (e.g., by palpating the carotid artery) in a short amount of time such as 10 seconds. See Eberle B. et al. "Checking the Carotid Pulse Diagnostic Accuracy of First Responders in Patients With and Without a Pulse," *Resuscitation* 33:107-116, 1996. Nevertheless, because time is of the essence in treating cardiac arrest, a caregiver may rush the preliminary evaluation, incorrectly conclude that the patient has no pulse, and proceed to provide therapy, such as defibrillation, when in fact the patient has a pulse. In other circumstances, the caregiver may incorrectly conclude that the patient has a pulse and erroneously withhold defibrillation therapy. A need therefore exists for a method and apparatus that quickly, accurately, and automatically determines whether a cardiac pulse is present in a patient, particularly to prompt a caregiver to provide appropriate therapy in an emergency situation.

SUMMARY OF THE INVENTION

The present invention provides pulse detection apparatus, software, and methods that use piezoelectric signal data obtained from a piezoelectric sensor placed on a patient's body. In a preferred embodiment, the piezoelectric sensor has a transducing element configured for placement on the surface of the patient's body. The piezoelectric sensor is adapted to sense movement in the patient's body due to a cardiac pulse and produce piezoelectric signal data in response thereto. Processing circuitry is configured to analyze the piezoelectric signal data for a feature indicative of the presence of a cardiac pulse. The processing circuitry then determines whether a cardiac pulse is present in the patient based on the feature.

A device constructed according to the invention may further comprise a display that automatically reports whether a cardiac pulse is present in the patient. The device may also include a defibrillation pulse generator that delivers a defibrillation pulse to the patient if the processing circuitry in the device determines that a cardiac pulse is not present in the patient.

In one aspect, the feature indicative of a cardiac pulse may be a temporal parameter. For example, the processing circuitry may determine a relative change in energy between a first energy in the piezoelectric signal data and a second energy in the piezoelectric signal data, the relative change in energy constituting the feature indicative of a cardiac pulse. In that regard, the first and second energy may be estimated using segments of piezoelectric signal data that are obtained at different times.

In another aspect, the feature indicative of a cardiac pulse may be a spectral parameter. In one exemplary implementation, the processing circuitry calculates an energy spectrum of the piezoelectric signal data and locates a peak energy in the energy spectrum. The energy value of the located peak is used as the feature indicative of a cardiac pulse. In another implementation, the frequency of a located peak energy is used as the feature indicative of a cardiac pulse. In either case, a cardiac pulse may be determined by comparing the feature with a predetermined threshold. Multiple features may also be obtained from the piezoelectric signal data and classified to determine the presence of a cardiac pulse.

In yet another aspect, electrocardiogram (ECG) signals may be used in the analysis of the piezoelectric signal data. A device constructed according to one implementation of the invention may determine whether a ventricular complex, such as a QRS complex, is present in the ECG data, and if so, select and analyze a segment of piezoelectric signal data corresponding in time to the detected venticular complex. In another implementation, the presence of a ventricular complex may be used to verify the detection of a cardiac pulse by determining whether a ventricular complex occurred in the ECG data within an expected time period in relation to the feature in the piezoelectric signal data that indicates a cardiac pulse. An ECG analysis may also be used to determine whether defibrillation pulse therapy is appropriate for a patient that is determined to be pulseless. In other applications, the device may recommend providing chest compressions or cardiopulmonary resuscitation (CPR) to the patient.

In yet another aspect, the feature indicative of the presence of a cardiac pulse may be obtained by comparing the piezoelectric signal data with a previously-identified piezoelectric signal data pattern known to predict the presence of a cardiac pulse. The comparison may produce a pattern match statistic that is compared with a predetermined pattern match threshold to determine whether a cardiac pulse is present.

In yet further implementations, ECG data obtained from the patient with the piezoelectric signal data may be used to assess the patient's cardiac activity. If, for instance, ventricular tachycardia is detected and the patient is determined to be pulseless, the device may prompt the delivery of defibrillation therapy to the patient. The device may be further configured to determine whether the patient is experiencing ventricular fibrillation, ventricular tachycardia, or asystole, and if the patient is not in a VF, VT, or asystole condition and is pulseless, the device may prompt delivery of electrotherapy designed specifically for pulseless electrical activity (PEA).

Embodiments of the invention intended for trained medical personnel may also provide a graph of the piezoelectric signal data that is representative of the presence or absence of a pulse in the patient. For example, the piezoelectric signal data may be shown as a waveform on a computer screen. The piezoelectric signal data may also be displayed as a bar whose length fluctuates according to the piezoelectric signal data. Other known display formats may also be used.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
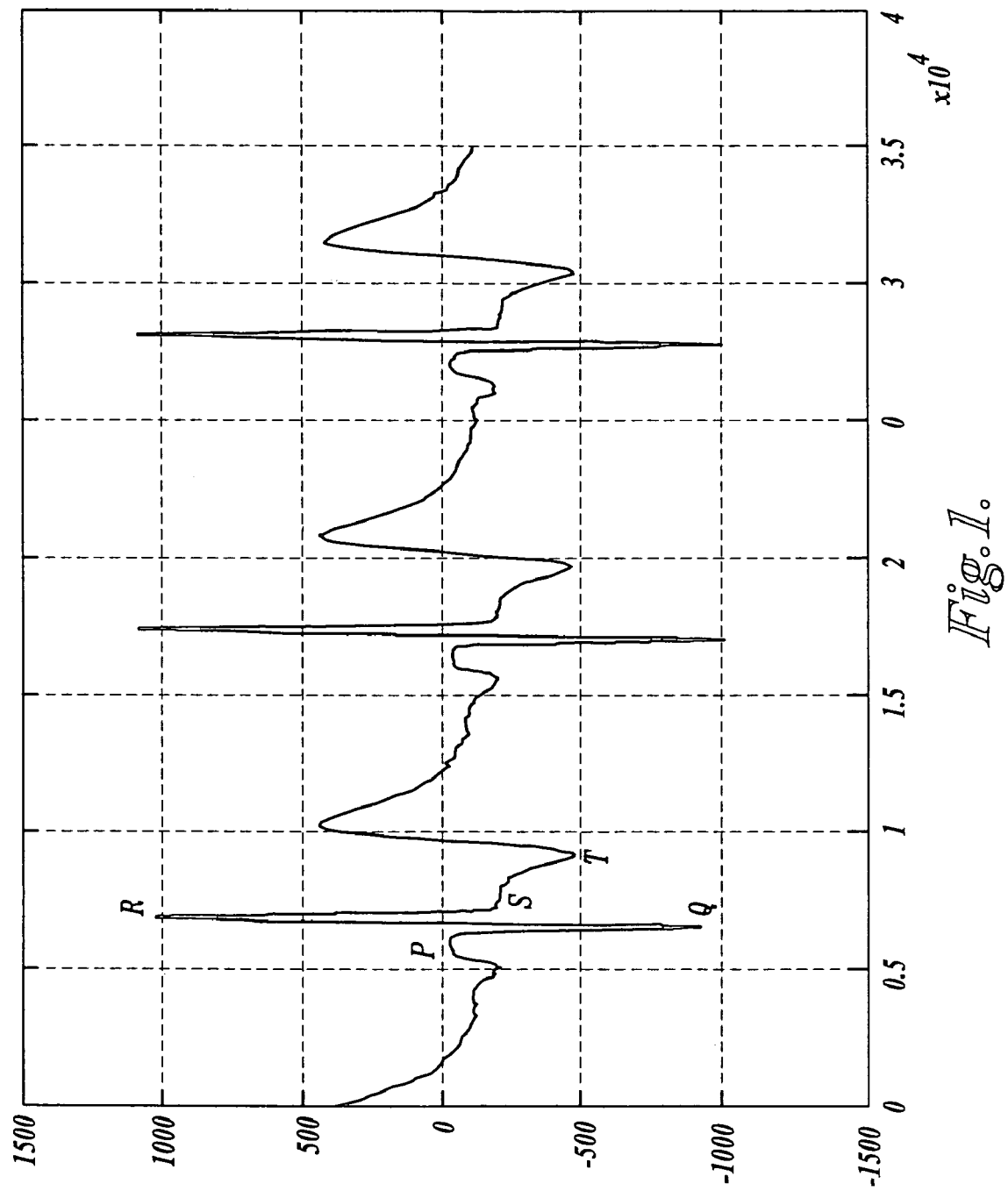
FIG. 1 is a graph depicting an electrocardiogram (ECG) waveform for three consecutive heartbeats of a human patient.

An electrocardiogram (ECG) waveform, as shown in FIG. 1, depicts the electrical activity of a patient's heart. A patient experiencing normal cardiac activity will exhibit an ECG waveform having standard identifiable features. The portion of the ECG waveform representing depolarization of the atrial muscle fibers is referred to as the "P" wave, as shown in FIG. 1. Depolarization of the ventricular muscle fibers is collectively represented by the "Q," "R," and "S" waves. Finally, the portion of the waveform representing repolarization of the ventricular muscle fibers is known as the "T" wave. Between heartbeats, a normal ECG waveform generally returns to an isopotential level.

The contraction and release of cardiac muscle in normal cardiac activity produces vibrations through the chest cavity that can be detected on the surface of the patient's body. Higher frequency vibrations from the opening and closing of the patient's heart valves are also detectable by equipment on surface of the patient's body. Conventionally, a physician listens to a patient's heartbeat by placing a stethoscope on the patient's chest. A transducer in the stethoscope senses the sound vibrations produced by the heart and delivers an acoustic signal that the physician can hear. Less technological but sometimes effective is simply to place a hand on the patient's chest. Although this does not substitute for checking the patient's pulse by palpating an appropriate pressure point (e.g., the carotid artery), vibrations in the chest wall may be detected.

The present invention is directed to a method and apparatus for cardiac pulse detection using an electric signal generated by a piezoelectric element placed on the patient's chest. Piezoelectricity is a phenomenon that has been recognized for many years. Early on, it was discovered that quartz, when subjected to an electric field, changes its dimensions. Conversely, quartz generates an electric signal when mechanically deformed. It was later discovered by researchers that certain ceramic materials could be made piezoelectric when the materials were first subjected to a high polarizing voltage.

Further research in this field discovered high piezo-activity in the polarized fluoropolymer Polyvinylidene fluoride (PVDF). While other polymers, such as PVC, exhibit a piezoelectric effect, PVDF and its copolymers have been found to be much more highly piezoelectric. New PVDF copolymers developed in recent years have expanded the applications of piezoelectric polymer sensors.

In the present invention, a sensor comprising a piezoelectric transducing element, such as PVDF, is placed on the chest of a patient. In one embodiment of the invention, the sensor is comprised of piezo film made of a PVDF polymer. Piezo film is a flexible and light weight plastic available in a wide variety of thicknesses and areas. Piezo film has electrical properties, such as a wide frequency range, low acoustic impedance, high voltage output, and high mechanical strength and impact resistance, that make it an excellent transducer. When placed on the surface of the patient's body, vibrations in the chest wall caused by the patient's heart cause the piezo film to produce electric signals. These electric signals are transmitted to processing circuitry that analyzes the signals to determine whether a cardiac pulse is indeed present in the patient.

Figure 2:
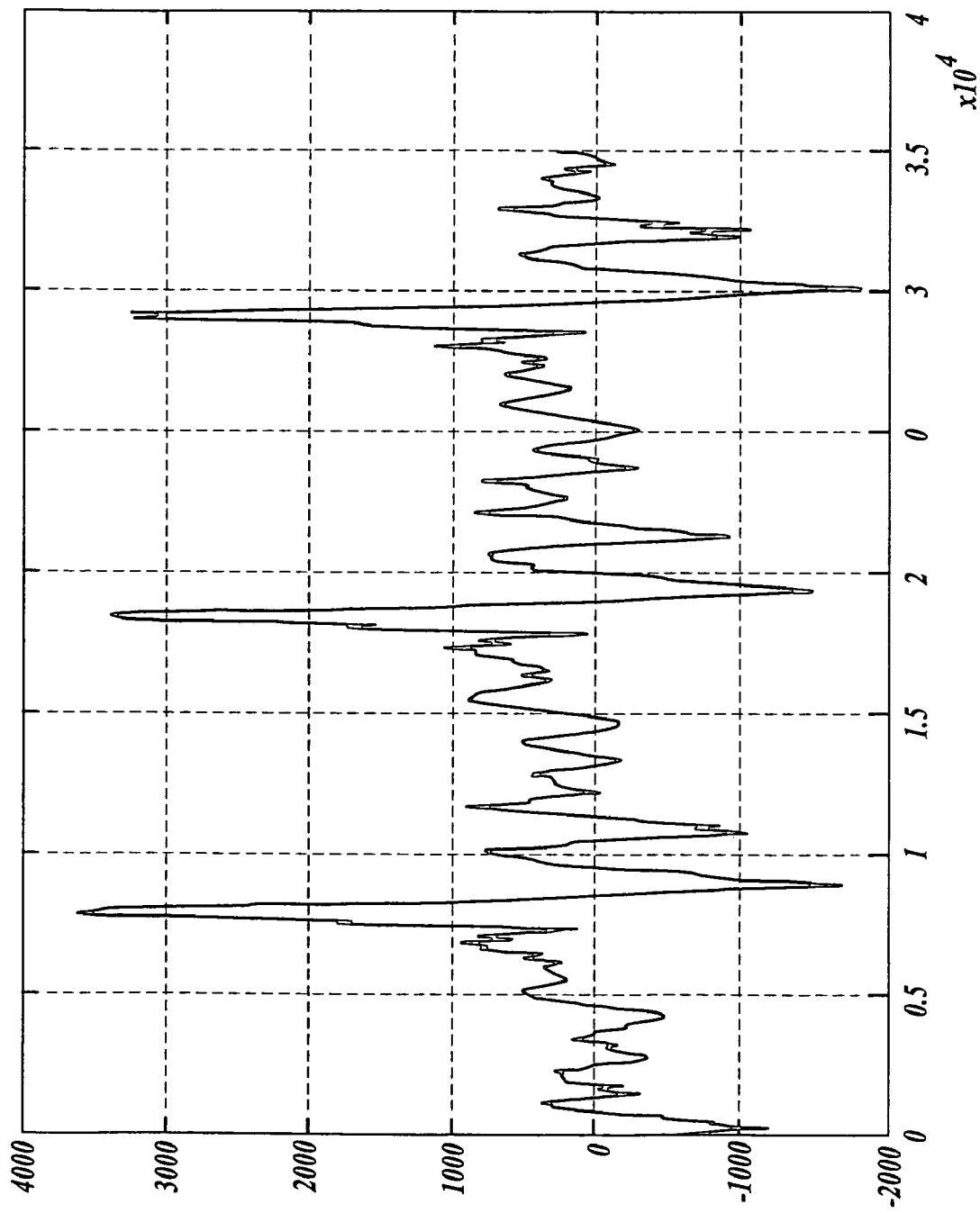
FIG. 2 is a graph depicting a piezoelectric signal waveform for three consecutive heartbeats of a human patient, in which the signal is obtained from a piezoelectric sensor placed on the surface of the patient's body.

FIG. 2 depicts a waveform of piezoelectric signal data obtained from a piezo film sensor placed on the chest of a patient. The timing of the piezoelectric signal data depicted in FIG. 2 correlates with the timing of the ECG data shown in FIG. 1. It is significant to note that the peak values in the piezoelectric signal data consistently occur following the QRS complexes depicted in the ECG data. It is thus evident that the piezoelectric signal data includes features, much as ECG data, that are indicative of the presence of a cardiac pulse in the patient.

Figure 3:
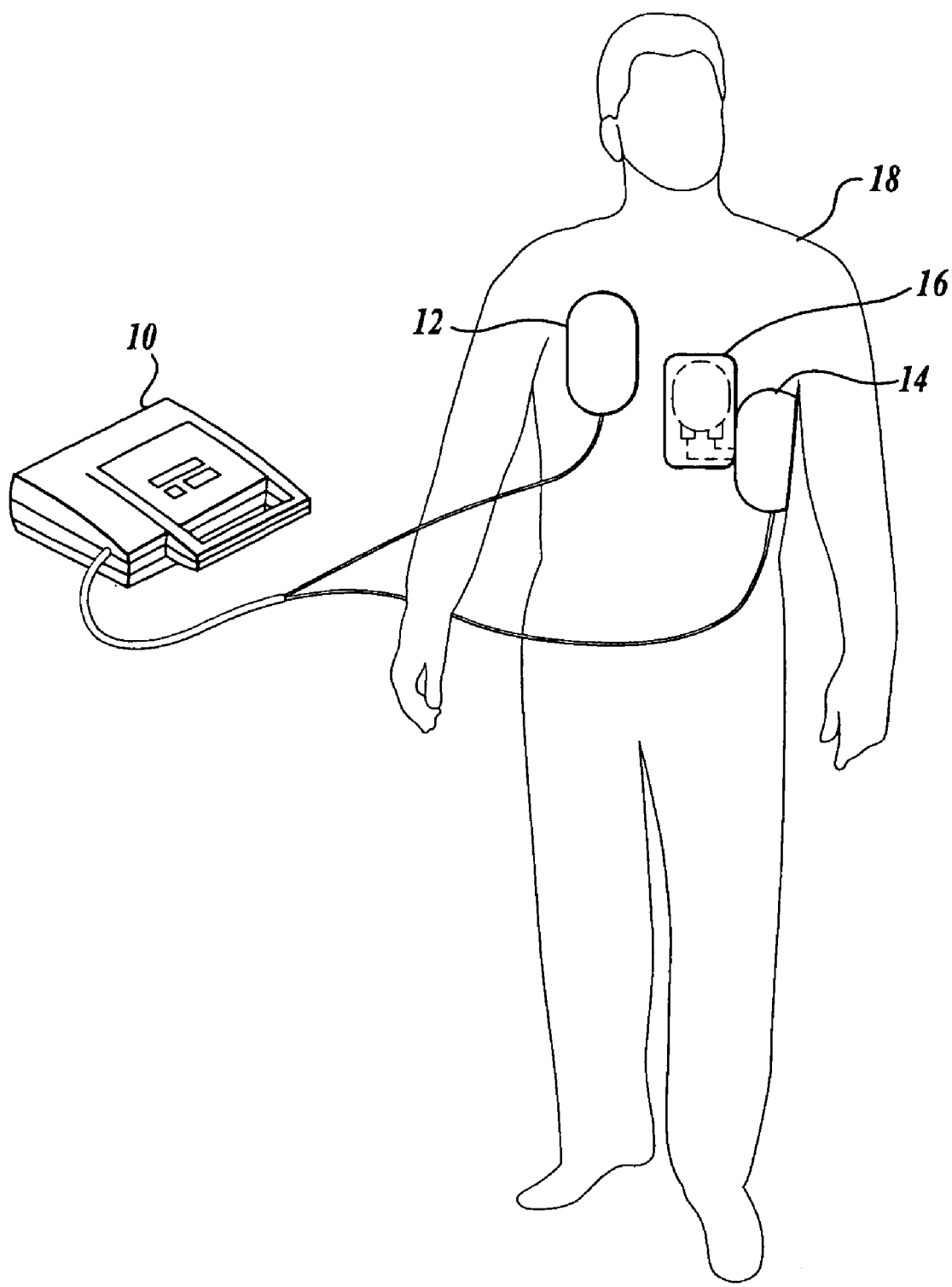
FIG. 3 is a pictorial diagram of a defibrillator, electrodes, and piezoelectric sensor constructed in accordance with one embodiment of the present invention and attached to a patient.

Although the present invention may be implemented in a variety of applications, it is particularly suited for use in a defibrillator, such as the defibrillator 10 shown in FIG. 3. In FIG. 3, the defibrillator 10 is shown connected to a patient 18 via defibrillation electrodes 12 and 14 placed on the skin of the patient 18. The defibrillator 10 uses the defibrillation electrodes 12 and 14 to deliver defibrillation pulses to the patient 18. The defibrillator 10 may also use the electrodes 12 and 14 to obtain ECG signals from the patient 18.

FIG. 3 further illustrates a piezoelectric sensor 16 placed on the patient 18. The piezoelectric sensor 16 is placed on the surface of the patient's body and is configured to detect cardiac vibrations in the chest wall of the patient. Vibrations sensed by the sensor 16 are converted by the defibrillator 10 into digital piezoelectric signal data for processing. The piezoelectric sensor 16 may be integrated with or attached to either or both of the electrodes 12 and 14. Alternatively, the sensor 16 may be attached to the patient 18 by one or more separate wires (not shown).

Figure 4A:
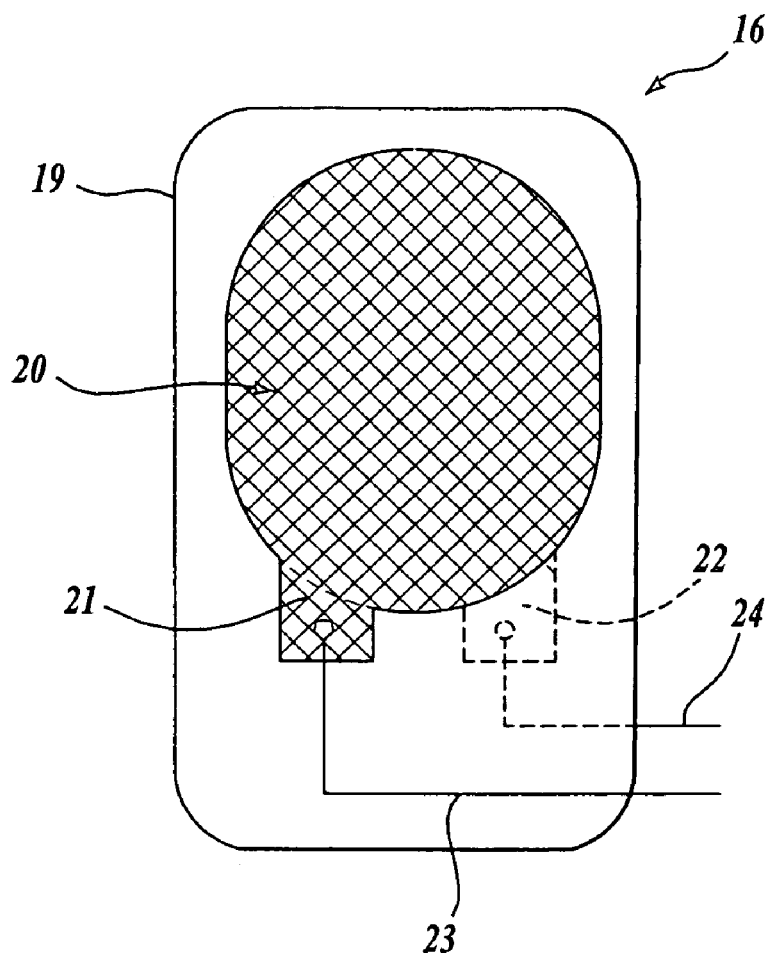
FIG. 4A is a plan view of one embodiment of a piezoelectric sensor as shown in FIG. 3.
Figure 4B:
FIG. 4B is a side cross-sectional view of the piezoelectric sensor shown in FIG. 4A.

FIGS. 4A and 4B illustrate the piezoelectric sensor 16 in greater detail. The piezoelectric sensor 16 is comprised of a sheet of piezo film material 19, preferably having a low thickness. The piezo film material 19 is disposed between two electrode elements 21 and 22. Piezo film having a low thickness results in a small cross-sectional area for the film. Thus, relatively small longitudinal forces (e.g., chest wall vibrations) create large stresses within the material 19, producing electrical signals that are received by the electrodes 21 and 22. Sensitivity to vibrations down to fractions of 1 Hz can be achieved using either conventional charge amplifiers or, where signal levels are relatively high, operation can be achieved using simple high impedance FET buffer circuits. Wires 23 and 24 respectively couple to offset tab locations of the electrodes 21 and 22 convey the piezoelectric signal to receiving device (e.g., the defibrillator 10 shown in FIG. 3).

The electrical energy output from the piezo film material 19 is generally proportional to the volume of the film that is stressed. Film thickness can be chosen to optimize the form of electrical signal produced. Mechanical strength considerations may also determine the film thickness. Thicker films generate higher voltages, but have smaller capacitance. In some circumstances, a laminate of thinner film with a compatible, passive material such as polyester, may be preferable to a single thicker film. Any area of film 19 that is not undergoing stress acts as a capacitive load on the "active" area and should be minimized where required. Persons having ordinary skill in the art will recognize that the layout of the piezoelectric sensor 16 depicted in FIGS. 4A and 4B is an exemplary design only. The dimensions, shape, and construction of the piezoelectric sensor 16 may be modified according to known techniques as required.

One useful model for considering the electrical characteristics of piezo film 19 is a strain-dependent voltage source in series with a capacitance. A resistive load added to the circuit will form a divider network with a simple RC high-pass filter characteristic. The cut-off frequency is given by $$f_o = \frac{1}{2\pi RC}$$

and the time constant $\tau = RC$. While application of a constant stress will generate an electrical signal having an initial level followed by an exponential decay, the piezoelectric sensor 16 is designed to detect vibrations in the patient's body. Such vibration cause the piezo film to produce an electric signal having a voltage that varies with the magnitude and frequency of the vibrations.

The active area of the sensor 16 is located between the electrodes 21 and 22 as indicated by the reference numeral 20. The particular shape of the electrodes 21 and 22 may be achieved during the piezo film manufacturing process by using screen printed conductive inks, metal masking during sputtered electrode deposition, or chemically etching the patterns by photolithographic techniques. To reinforce the connection of the wires 23 and 24 to the electrodes 21 and 22, crimps, eyelets, or rivets that penetrate through the film at each of the offset tab locations may be used. The attachment area may also be reinforced with polyester. Additional information regarding materials and techniques for constructing piezo film sensors is available from Measurement Specialties, Inc. of Valley Forge, Pa. See e.g., "Piezo Film Sensors Technical Manual," Internet version, August 1998, from Measurement Specialties, Inc., the content of which is incorporated by reference herein.

Figure 5:
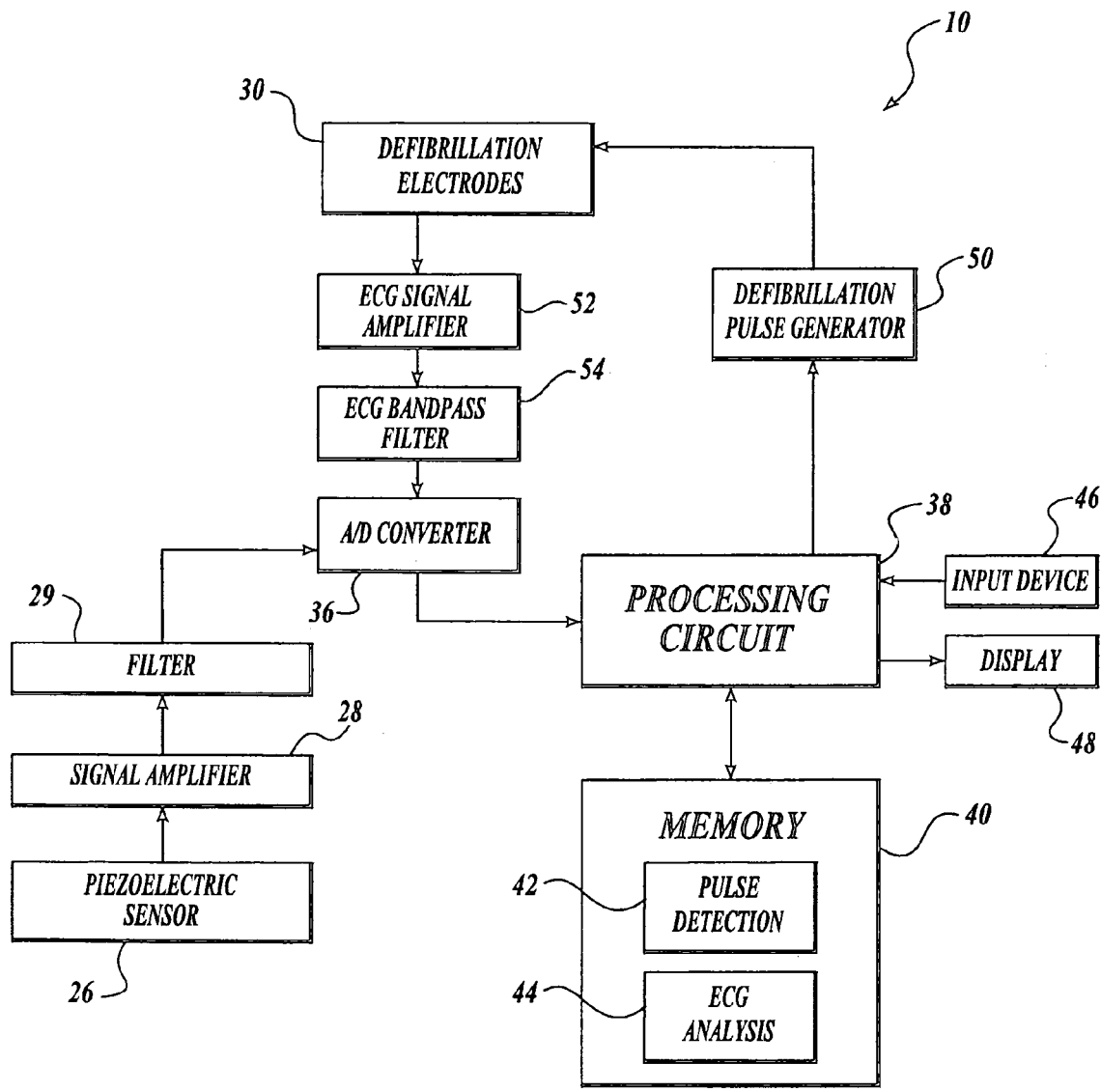
FIG. 5 is a block diagram of major components of a defibrillator as shown in FIG. 3.

Prior to discussing various pulse detection processes that the defibrillator 10 may implement in accordance with the present invention, a brief description of certain major components of the defibrillator 10 is provided. Referring now to FIG. 5, the defibrillator 10 includes defibrillation electrodes 30 (e.g., electrodes 12, 14 described above in FIG. 3). A piezoelectric sensor 26 (e.g., sensor 16 shown in FIG. 3)

placed on the chest of the patient produces electric signals in response to movement of the chest wall. A signal amplifier 28 receives the piezoelectric signal from the sensor 26 and amplifies the signal as appropriate for digitization by analog-to-digital (A/D) converter 36. Prior to A/D conversion, a filter 29 may be used to filter the amplified piezoelectric signal to emphasize the portion of the signal that most closely reveals chest wall movement due to cardiac pulses in the patient.

The filtered piezoelectric signal is delivered to the A/D converter 36 which converts the signal into digital piezoelectric signal data for further evaluation. The filter 29 or other filters (not shown) may also be provided to reduce any aliasing introduced in the piezoelectric signal by the A/D converter 36. The parameters of such filtering depend, in part, on the sampling rate of the A/D converter. Antialiasing filters, as well as A/D converters, are well-known in the art, and may be implemented in hardware or software, or a combination of both. For example, an embodiment of the invention may use a hardware lowpass filter on the piezoelectric signal before the A/D converter 36, and then a software highpass filter on the digital piezoelectric signal data after the A/D conversion. An additional software lowpass filter after the A/D conversion may also be used to further limit the bandwidth of the piezoelectric signal data. In any respect, the A/D converter 36 delivers the digital piezoelectric signal data to a processing circuit 38 for evaluation.

The processing circuit 38 evaluates the piezoelectric signal data for a feature indicating the presence of a cardiac pulse. The processing circuit 38 is preferably comprised of a computer processor that operates in accordance with programmed instructions stored in a memory 40 that implement a pulse detection process 42, described in more detail below. The processing circuit 38 may also store in the memory 40 the piezoelectric signal data obtained from the patient, along with other event data and ECG signal data. The memory 40 may be comprised of any type or combination of types of storage medium, including, for example, a volatile memory such as a dynamic random access memory (DRAM), a non-volatile static memory, or computer-readable media such as a magnetic tape or disk or optical storage unit (e.g., CD-RW or DVD) configured with permanent or removable media.

The processing circuit 38 may report the results of the pulse detection process to the operator of the defibrillator 10 via a display 48. The processing circuit 38 may also prompt actions (e.g., CPR) to the operator to direct the resuscitation effort. The display 48 may include any kind of output device, for example, lights, audible signals, alarm, printer, or display screen. The processing circuit 38 may also receive input from the operator of the defibrillator 10 via an input device 46. The input device 46 may include one or more keys, switches, buttons, dials, or other types of user input devices.

The defibrillation electrodes 30 may further be used to sense the patient's electrocardiogram (ECG) signals. ECG signals obtained from the patient are amplified by the ECG signal amplifier 52 and filtered by the ECG bandpass filter 54 in a conventional manner. The A/D converter 36 converts the ECG signals into digitized ECG data and provides the ECG data to the processing circuit 38 for evaluation.

Preferably, the processing circuit 38 evaluates the ECG signals in accordance with programmed instructions 44 stored in the memory 40 that carry out an ECG evaluation process to determine whether a defibrillation shock should be provided. A suitable method for determining whether to apply a defibrillation shock is described in U.S. Pat. No. 4,610,254, which is assigned to the assignee of the present invention and incorporated by reference herein. If the processing circuit 38 determines that immediate delivery of a defibrillation pulse is appropriate, the processing circuit 38 instructs a defibrillation pulse generator 50 to prepare to deliver the defibrillation pulse to the patient. In that regard, the defibrillation pulse generator 50 uses an energy source (e.g., a battery) to charge one or more defibrillation capacitors in the defibrillator 10.

When the defibrillation charge is ready for delivery, the processing circuit 38 advises the operator via the display 48 that the defibrillator 10 is ready to deliver the defibrillation pulse. The processing circuit 38 may ask the operator to initiate the delivery of the defibrillation pulse. When the operator initiates delivery of the defibrillation pulse (e.g., via the input device 46), the processing circuit 38 instructs the defibrillation pulse generator 50 to discharge through the patient the energy stored in the defibrillation capacitors (via the defibrillation electrodes 30). Alternatively, the processing circuit 38 may cause the defibrillation pulse generator 50 to automatically deliver the defibrillation pulse when specified conditions (e.g., expiration of a predetermined period of time, acceptable measured patient impedance, etc.) are met.

In some circumstances, it may be preferable to apply CPR to the patient before defibrillation even though cardiac conditions, such as VF, are detected, especially for patients in whom defibrillation is initially unlikely to succeed. See L. Cobb et al., "Influence of Cardiopulmonary Resuscitation Prior to Defibrillation in Patients with Out-of-Hospital Ventricular Fibrillation" *JAMA* 281:1182-1188 (1999), incorporated by reference herein. Thus, if desired, the defibrillator 10 may recommend the application of chest compressions or CPR in situations where a cardiac pulse is not detected and the ECG reveals a cardiac rhythm for which immediate treatment by defibrillation therapy is not indicated.

While FIG. 5 illustrates certain major components of the defibrillator 10, those having ordinary skill in the art will appreciate that the defibrillator 10 may contain more or fewer components than those shown. The disclosure of a preferred embodiment of the defibrillator 10 does not require that all of the general conventional components be shown. It will further be appreciated that aspects of the invention may be implemented in a cardiac monitor having essentially the same components as the defibrillator 10 shown in FIG. 5, except that the cardiac monitor does not have the components necessary for delivering a defibrillation pulse. Furthermore, some or all of the programmed instructions 42 and 44 may be implemented in hardware as an alternative to software instructions stored in the memory 40.

In any event, it is evident to one having ordinary skill in the art that the present invention may be implemented by one or more devices that include logic circuitry. The one or more devices perform functions and/or methods as are described herein. The logic circuitry may include a processor, such as the processing circuit 38, that may be programmable for a general purpose, or dedicated, such as a microcontroller, a microprocessor, a digital signal processor (DSP), etc. For example, a device implementing the invention may be a digital computer-like device, such as a general purpose computer selectively activated or reconfigured by a computer program stored in the computer. Alternatively, the device may be implemented as an application specific integrated circuit (ASIC), etc.

The invention additionally provides methods and algorithms that are described below. The methods and algorithms presented herein are not necessarily inherently associated with any particular computing device or other apparatus. Rather, various general purpose machines may be used with programs in accordance with the teachings herein, or it may prove more convenient to construct more specialized apparatus to perform the required method steps. The required structure for a variety of these machines becomes apparent from this description.

In all cases, it should be borne in mind the distinction between the method of the invention itself and the method of operating a computing machine. The present invention relates to both methods in general, and also to steps for operating a computer and for processing electrical or other physical signals to generate other desired physical signals.

The invention additionally provides programs and methods of program operation. A program is generally defined as a group of steps leading to a desired result. A program made according to an embodiment of the invention is most advantageously implemented as a program for a computing machine, such as a defibrillator 10 or other equipment housing a general purpose computer, a special purpose computer, a microprocessor, etc.

The invention also provides storage media that, individually or in combination with others, have stored thereon instructions of a program made according to the invention. A storage medium according to the invention is a computer-readable medium, such as a memory 40 as noted above, and is read by the computing machine mentioned above.

It is readily apparent that the steps or instructions of a program made according to an embodiment of the invention requires physical manipulations of physical quantities. Usually, though not necessarily, these quantities may be transferred, combined, compared, and otherwise manipulated or processed according to the instructions, and they may also be stored in a computer-readable medium. These quantities include, for example, electrical, magnetic, and electromagnetic signals, and also states of matter that can be queried by such signals. It is convenient at times, principally for reasons of common usage, to refer to these quantities as signal data, bits, data bits, samples, values, symbols, characters, images, terms, numbers, or the like. It should be borne in mind, however, that all these and similar terms are associated with the appropriate physical quantities, that these terms are merely convenient labels applied to these physical quantities.

This detailed description is presented largely in terms of flowcharts, display images, algorithms, processes, and symbolic representations of operations of data bits within at least one computer readable medium. The present description achieves an economy in that a single set of flowcharts is used to describe both methods of the invention and programs according to the invention. Such descriptions and representations are the type of convenient labels used by those skilled in programming and/or data processing arts to effectively convey the substance of their work to others skilled in the art. A person skilled in the art of programming may use these descriptions to readily generate specific instructions for implementing a program according to the present invention.

Often, and for the sake of convenience only, it is preferred to implement and describe a program as various interconnected distinct software modules or features, individually and collectively also known as software, though such modules may equivalently be aggregated into a single program with unclear boundaries. The software modules or features of the present invention may be implemented by themselves, or in combination with others. Although the program may be stored in a computer-readable medium, such as a memory 40, a person skilled in the art will readily recognize that it need not be a single memory, or even a single machine. Various portions, modules, or features of the program may reside in separate memories, or even separate machines. The separate machines may be connected directly, or through a network, such as a local area network (LAN), or a global network, such as the Internet, by wired or wireless connections. For example, a data acquisition unit may collect the piezoelectric signal data obtained in the present invention and communicate the data to a remote computing machine for analysis and report whether a cardiac pulse is present.

It will be appreciated that some of the methods described herein may include software steps that can be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is performed in which plane.

In any event, in the present case, methods of the invention are implemented by machine operations. In other words, embodiments of programs of the invention are made such that they perform methods of the invention that are described in this document. These may optionally be performed in conjunction with one or more human operators performing some, but not all of them. As per the above, these need not be co-located with each other, but each only with a machine that houses a portion of the program. Alternatively, some of these machines may operate automatically, without users and/or independently from each other.

Methods of the invention are now described. In one aspect, a pulse detection process conducted in accordance with the present invention analyzes the patient's piezoelectric signal data to determine whether chest wall movement due to a cardiac pulse is present in the patient. Characteristic vibrations of the patient's chest are used as an indication of the presence of a cardiac pulse in the patient. In another aspect, the pulse detection process may analyze multiple physiological signals. For example, the pulse detection process may analyze phonocardiogram (PCG) data for heart sounds and impedance signal data for characteristic fluctuations in patient impedance, combined with the piezoelectric signal data described herein, to determine the presence of a cardiac pulse. See, e.g., the processing described in the copending U.S. Patent Application titled PULSE DETECTION APPARATUS, SOFTWARE, AND METHODS USING PATIENT PHYSIOLOGICAL SIGNALS, filed concurrently herewith under Ser. No. 13/272,733, and incorporated by reference herein. A combination of analyzed physiological signals may advantageously provide a more robust pulse detection process with improved detection characteristics.

Figure 6:
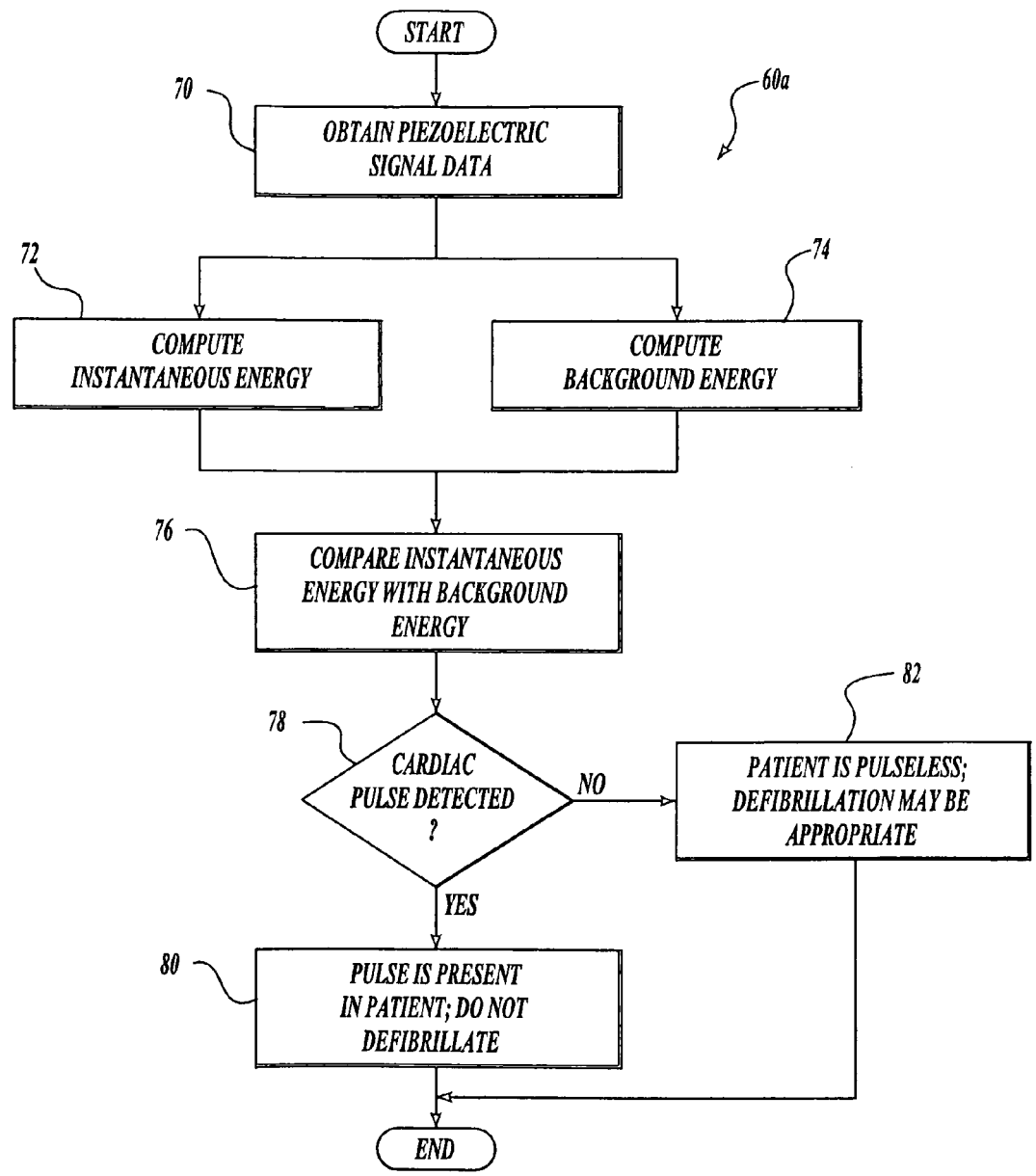
FIG. 6 is a flow diagram of a pulse detection process performed by a defibrillator as shown in FIG. 3, in which an analysis of temporal energy in piezoelectric signal data obtained from a patient is performed.

FIG. 6 illustrates a pulse detection process 60a that analyzes a temporal energy in the piezoelectric signal data. The pulse detection process 60a begins at block 70 by obtaining piezoelectric signal data from a patient. As noted earlier, piezoelectric signals received from a piezoelectric sensing device (e.g., sensor 16 in FIG. 3) placed on the patient are converted into digital piezoelectric signal data.

The pulse detection process 60a evaluates the piezoelectric signal data for at least one feature indicative of the presence of a cardiac pulse. In blocks 72 and 74, the pulse detection process 60a calculates estimates of the instantaneous energy and background energy in the piezoelectric signal data. The estimated instantaneous energy may be calculated in block 72 simultaneously with, before, or after, the calculation of estimated background energy in block 74.

In block 72, the estimated instantaneous energy may be calculated using a set of piezoelectric signal data obtained from the patient during a predetermined time window. One exemplary embodiment of the invention uses a time window of 20 milliseconds in length, though a longer, shorter, or shifted time window may be used for estimating the instantaneous energy. The estimated instantaneous energy may be calculated by squaring and summing each of the piezoelectric data values in the predetermined time window.

The estimated background energy is calculated in block 74, preferably using a set of piezoelectric signal data obtained in an earlier predetermined time window. One exemplary embodiment of the invention calculates the estimated background energy using piezoelectric signal data in a 100 millisecond time window commencing 220 milliseconds prior to the current time. The piezoelectric signal data within the earlier time window may also be squared and summed to produce the estimated background energy. Furthermore, other time window lengths and starting points may be used.

The estimated instantaneous energy and background energy are compared at block 76 to determine a relative change in energy in the piezoelectric signal data. The relative change in energy is used by the pulse detection process 60*a* as a feature indicative of the presence of characteristic chest vibrations, and hence the presence of a cardiac pulse. If the relative change in energy between the estimated instantaneous energy and the estimated background energy exceeds a predetermined threshold, the pulse detection process 60*a* determines that a cardiac pulse was present. Because the calculation of background energy uses piezoelectric signal data obtained in a time window earlier than the piezoelectric signal data used to calculate instantaneous energy, the rise and fall of the background energy waveform is expected to generally follow the rise and fall of the instantaneous energy waveform. Note that the background and instantaneous energies should previously be normalized for purposes of comparison to each other. For example, if squaring and summing is used and one energy uses a 100 ms time window and the other energy uses a 20 ms time window, the result of the energy using a 100 ms time window should be divided by 5 so it can be properly compared against the result from a 20 ms time window.

In decision block 78, if a cardiac pulse was detected, the pulse detection process 60*a* proceeds to block 80 and reports the presence of a cardiac pulse in the patient (thus indicating that defibrillation therapy for the patient is not advised). Otherwise, if a cardiac pulse was not detected, the pulse detection process 60*a* determines in block 82 that the patient is pulseless and that defibrillation therapy may be appropriate. A defibrillator 10 implementing the pulse detection process 60*a* may proceed to determine whether defibrillation therapy is appropriate, e.g., by obtaining and processing ECG data from the patient as described in U.S. Pat. No. 4,610,254, referenced earlier and incorporated herein by reference.

In a further embodiment of the invention, the pulse detection process 60*a* may be repeated over a specified time interval or for a specified number of repetitions to produce a series of determinations of whether a cardiac pulse is present in the patient. The time windows for computing the estimated instantaneous energy and background energy are shifted to correspond with each instance of time in which the pulse detection process 60*a* is performed. The pulse detection process 60*a* may require a specified number of pulse detections before determining that a cardiac pulse is in fact present in the patient.

During the time in which the instantaneous energy exceeds the background energy by a predetermined threshold, the comparison may return a "1", signifying the detection of a cardiac pulse. The predetermined threshold may be adjusted to achieve a desired sensitivity and specificity of detection. When the relative change in energy between the instantaneous energy and the background energy does not exceed the predetermined threshold, the comparison may return a "0", signifying that a cardiac pulse has not been detected.

Figure 7:
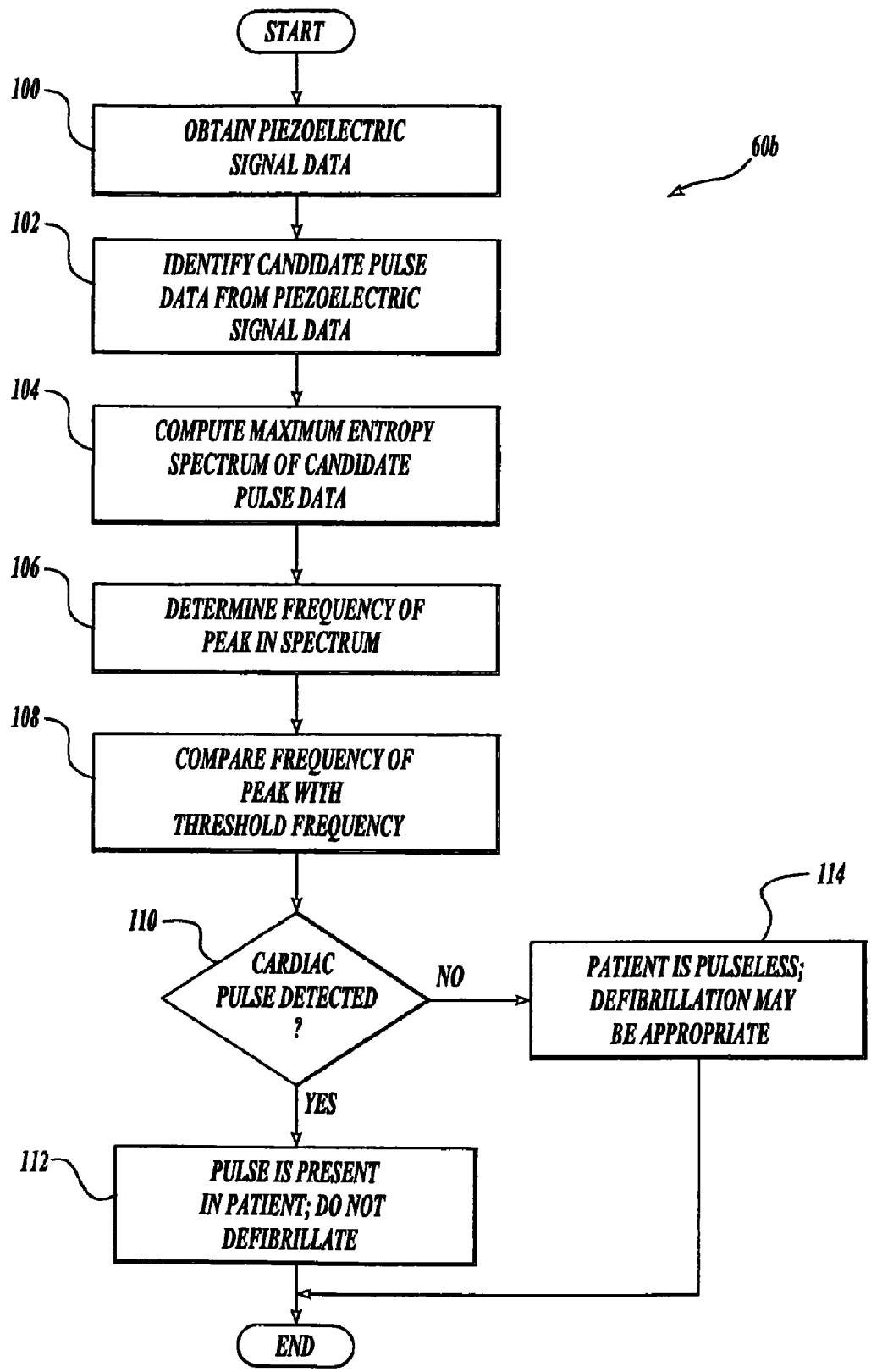
FIG. 7 is a flow diagram of another pulse detection process performed by a defibrillator as shown in FIG. 3, in which a spectral peak frequency analysis of piezoelectric signal data is performed.

FIG. 7 illustrates another pulse detection process 60*b*. As with the detection process 60*a*, the detection process 60*b* analyzes piezoelectric signal data to detect the presence of characteristic chest vibrations, and hence a cardiac pulse, in a patient. The detection process 60*b*, however, focuses on a spectral energy analysis of the piezoelectric signal data (as compared to the temporal energy analysis performed in the detection process 60*a*).

The pulse detection process 60*b* begins at block 100 by obtaining piezoelectric signal data from the patient in a manner as discussed above with respect to block 70 (FIG. 6). In block 102, the piezoelectric signal data is preferably analyzed to identify a set of piezoelectric signal data that likely contains information identifying the presence of a cardiac pulse. In that regard, the candidate piezoelectric data may be identified by using the temporal energy comparison discussed in block 76 of the pulse detection process 60*a*. When the estimated instantaneous energy exceeds the estimated background energy by a predetermined threshold, the energy comparison suggests that a cardiac pulse has been detected. Alternatively, a set of piezoelectric signal data potentially identifying a cardiac pulse may be selected by evaluating the patient's ECG data for the occurrence of an R-wave. The timing of cardiac pulse vibrations in the patient's chest in relation to an R-wave is generally known in the art and may be used to predict the timing of candidate data in the piezoelectric signal data. Other embodiments of the invention may compute an energy spectrum without first identifying candidate piezoelectric data, e.g., by continuously computing an energy spectrum using the most current piezoelectric data as the candidate data.

Next, in block 104, the pulse detection process 60*b* computes an energy spectrum of the candidate piezoelectric signal data, preferably using a maximum entropy method, though other spectral calculations may be used. Computing an energy spectrum using a maximum entropy method ("MEM spectrum") is well-known in the art. See, e.g., *Modern Spectral Estimation: Theory and Application*, by Stephen M. Kay, published by Prentice Hall of Englewood Cliffs, N.J., beginning at p. 182, and incorporated herein by reference. An MEM spectrum typically appears smoother than an energy spectrum produced by Fourier transform techniques. The MEM spectrum may be normalized by removing a baseline (e.g., DC) energy value across the MEM spectrum.

The frequency of a peak energy value in the energy spectrum may be used as a feature indicative of the presence of a cardiac pulse. The frequency of the selected peak is evaluated against a predetermined threshold frequency value to decide whether a cardiac pulse has been detected. In block 106 (FIG. 7), the pulse detection process 60*b* evaluates the energy values in the MEM spectrum to identify a peak value in the MEM spectrum and determine its frequency.

In block 108, the frequency of the peak value is compared with a predetermined threshold frequency to decide whether a cardiac pulse is detected. For example, if the frequency of the peak is less than or equal to a threshold frequency, e.g., 100 Hz, the pulse detection process 60*b* determines that a cardiac pulse was detected. Alternative embodiments of the invention may use values other than 100 Hz for the predetermined threshold frequency.

If a cardiac pulse was detected, the pulse detection process 60*b* proceeds from decision block 110 to block 112 and determines that a pulse is present in the patient, thus advising against application of a defibrillation pulse. If, in decision block 110, a cardiac pulse was not detected, the pulse detection process 60b determines in block 114 that the patient is pulseless and that defibrillation may be appropriate for the patient. In that case, further signal processing of ECG data obtained from the patient is preferably performed to determine the applicability of defibrillation therapy, e.g., as described in U.S. Pat. No. 4,610,254, referenced earlier. In some circumstances, CPR therapy is warranted.

Figure 8:
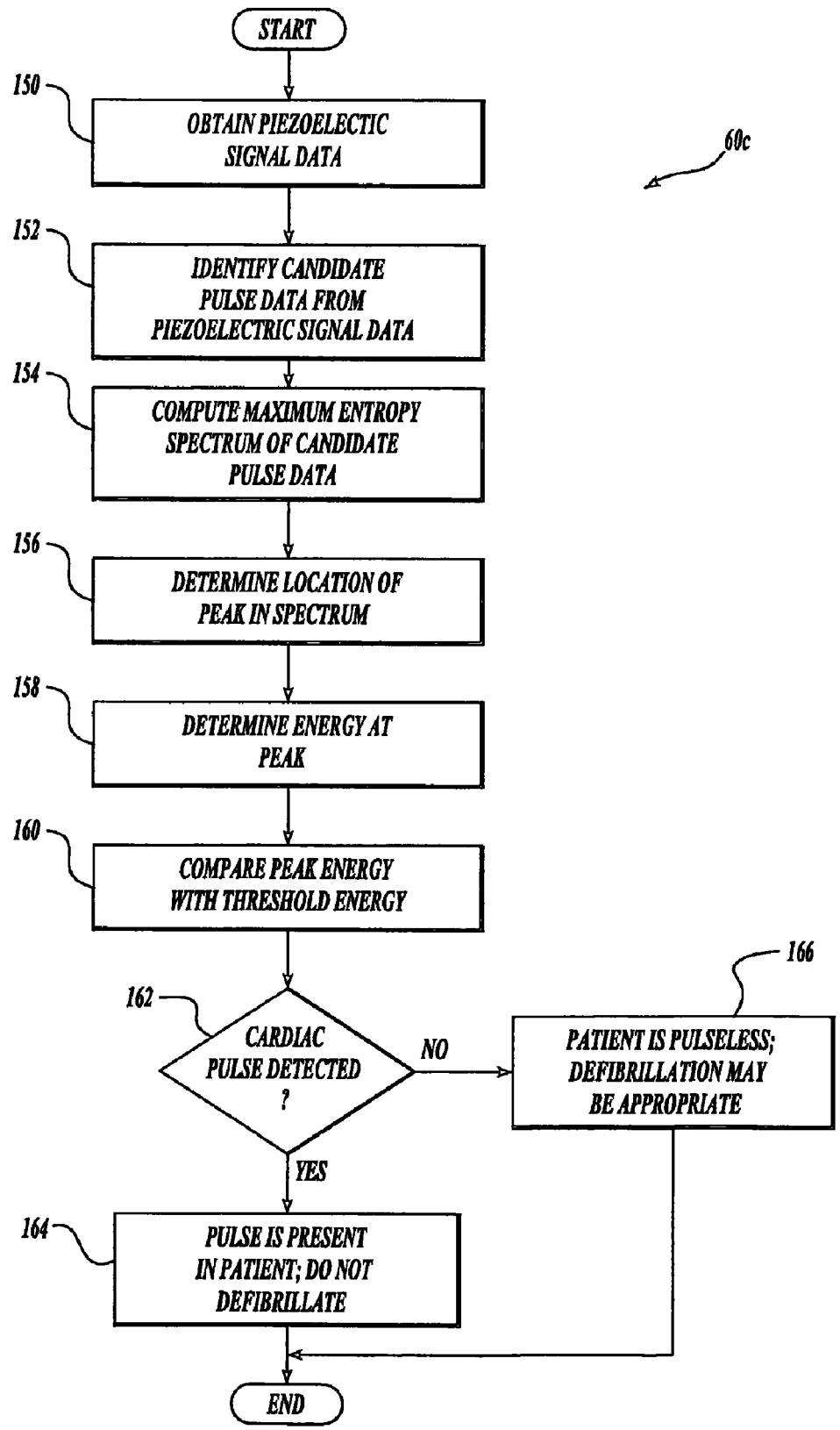
FIG. 8 is a flow diagram of another pulse detection process performed by a defibrillator as shown in FIG. 3, in which a spectral peak energy analysis of piezoelectric signal data is performed.

FIG. 8 illustrates another pulse detection process 60c that also uses an MEM spectrum as calculated in block 104 of the detection process 60b. Instead of analyzing the frequency of a peak value in the MEM spectrum, as performed in the process 60b, the process 60c analyzes the energy of a peak value in the MEM spectrum.

The detection process 60c begins at block 150 by obtaining piezoelectric signal data from the patient in a manner as discussed earlier with respect to block 70 (FIG. 6). The piezoelectric signal data is analyzed in block 152 to identify candidate piezoelectric signal data corresponding to the time when a cardiac pulse likely occurred. The analysis performed in block 152 may include an energy comparison process or ECG analysis as described earlier with respect to block 102 of pulse detection process 60b (FIG. 7). An MEM spectrum of the candidate piezoelectric signal data is then computed in block 154 in a manner as discussed earlier with respect to block 104 (FIG. 7). Also, as noted before, the energy spectrum calculation process may be run continuously.

In block 156, the pulse detection process 60c evaluates the energy values in the MEM spectrum to locate a peak value in the spectrum. The energy value of the peak, determined in a block 158, is used as a feature indicative of the presence of a cardiac pulse, and is compared in block 160 with a predetermined threshold energy to decide whether a cardiac pulse was detected. If the energy of the peak value exceeds the threshold energy, the pulse detection process 60c determines in decision block 162 that a cardiac pulse was detected.

If, in decision block 162, a cardiac pulse was detected, the pulse detection process 60c proceeds to block 164 and determines that a cardiac pulse is present in the patient. In that circumstance, the detection process 60c may advise against providing defibrillation therapy to the patient. The detection process may also advise to check patient breathing. On the other hand, if a cardiac pulse was not detected in decision block 162, the pulse detection process 60c proceeds to block 166 and determines that the patient is pulseless. In that circumstance, the detection process 60c advises that defibrillation therapy may be appropriate for the patient. In other embodiments, a prompt that advises the application of chest compressions or CPR may be given in addition to or in place of advising defibrillation therapy for pulseless patients. An analysis of ECG data, as noted earlier, may be used to determine the applicability of defibrillation therapy.

On occasion, it is possible that noise in the piezoelectric signal data may cause a false detection of what appears to be characteristic chest vibrations, and hence false detection of a cardiac pulse, when using one of the detection processes 60 described herein. If the signal-to-noise ratio of the piezoelectric signal data obtained from the patient is not high enough to avoid such false detection of a cardiac pulse, the pulse detection processes 60 may be combined in one or more ways to produce a pulse detection process with improved specificity. For example, FIG. 9 illustrates a detection process 60d that combines aspects of the detection processes 60a, 60b, and 60c.

Figure 9:
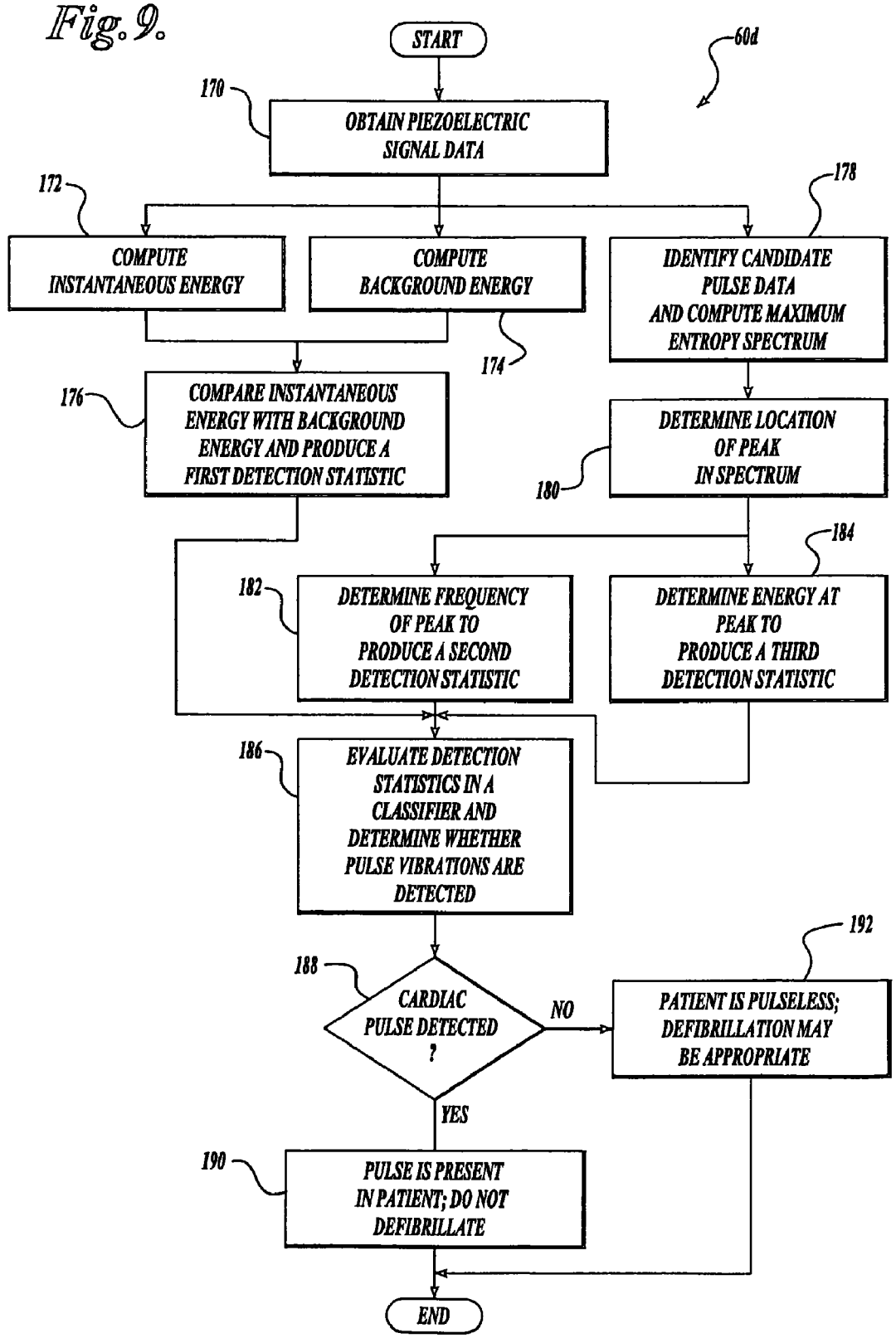
FIG. 9 is a flow diagram of yet another pulse detection process performed by a defibrillator as shown in FIG. 3 that incorporates aspects of the pulse detection processes shown in FIGS. 6, 7 and 8.

In FIG. 9, the pulse detection process 60d begins at block 170 by obtaining piezoelectric signal data from a patient, e.g., in a manner as described earlier with respect to block 70 of pulse detection process 60a (FIG. 6). After the piezoelectric signal data is obtained, estimates of the instantaneous energy and the background energy in the piezoelectric signal data are computed in blocks 172 and 174, e.g., in a manner as described earlier with respect to blocks 72 and 74. The estimated instantaneous and background energy values are then compared in a block 176, e.g., as described earlier with respect to block 76, to produce a first detection statistic, or feature, indicative of the presence of a cardiac pulse. The first detection statistic produced in block 176 is provided to a multidimensional classifier in block 186 that evaluates detection statistics to determine whether a cardiac pulse has been detected. Alternatively, the instantaneous and background energies computed in blocks 172 and 174 may be directly provided as separate detection statistics to the multidimensional classifier in block 186 for joint classification with any other detection statistics provided to the classifier (i.e., eliminating the comparison performed in block 176).

The piezoelectric signal data obtained in block 170 is also used in identifying candidate data that is likely indicative of a cardiac pulse and for computing an MEM spectrum of the candidate data in block 178, in a manner as described earlier with respect to blocks 102 and 104 of pulse detection process 60b (FIG. 7). Once the MEM spectrum is computed, the pulse detection process 60d in block 180 locates a peak value in the MEM spectrum.

The frequency of the peak value is determined in a block 182 and provided as a second detection statistic, or feature, to the classifier in block 186. Alternatively, the second detection statistic may be the result of comparing the frequency of the peak value with a threshold frequency, e.g., in a manner as described earlier with respect to block 108 (FIG. 7), to produce the second detection statistic.

In block 184, the pulse detection process 60d also determines the energy at the peak value and provides the energy value as a third detection statistic, or feature, to the classifier in block 186. The peak energy value may alternatively be compared with a threshold energy, e.g., in a manner as described earlier with respect to block 160 (FIG. 8), to produce the third detection statistic.

The classifier in block 186 jointly classifies the first, second, and third detection statistics using a multidimensional classifier to determine whether a cardiac pulse is present in the patient. Techniques for constructing multidimensional classifiers are well-known in the art. For an expanded description of classifiers suitable for use in the present invention, see, e.g., R. Duda and P. Hart, *Pattern Classification and Scene Analysis*, published by John Wiley & Sons, New York, and incorporated herein by reference.

The classifier in block 186 may also use a voting scheme to determine whether a cardiac pulse is present in the patient. For example, if any of the first, second, or third detection statistics indicates the detection of a cardiac pulse (e.g., the instantaneous energy exceeded the background energy by a threshold value, the frequency of a peak was equal to or less than a threshold frequency, or the energy of the second peak exceeded a threshold energy), the classifier may determine that a pulse is present in the patient. Alternatively, the classifier in block 186 may determine that a pulse is present by finding that a combination of the first, second, and third detection statistics is indicative of the presence of a cardiac pulse (e.g., a positive indication from the first detection statistic combined with a positive indication from the second or third detection statistics, etc.). The classifier in block 186 may also weight the first, second, or third detection statistics to emphasize one detection statistic over another in deciding whether a cardiac pulse is present.

If, in decision block 188, a cardiac pulse was detected, the pulse detection process 60*d* determines in block 190 that a pulse is present in the patient and may advise the operator of the defibrillator to not defibrillate the patient. The process may also advise to not perform CPR, in connection with or in place of any defibrillation advice. Otherwise, if a cardiac pulse was not detected in decision block 188, the pulse detection process 60*d* determines in block 192 that the patient is pulseless and that CPR/chest compressions and/or defibrillation therapy may be appropriate. An analysis of ECG data, as described earlier in reference to U.S. Pat. No. 4,610,254, may be used to determine whether defibrillation therapy is appropriate.

An analysis of ECG data may also be combined with an analysis of piezoelectric signal data to determine the presence of a cardiac pulse in the patient. In one aspect, detecting a QRS complex, or other ventricular complex, in the ECG data in time relation to the occurrence of a characteristic feature in the piezoelectric signal data may serve to confirm the detection of a cardiac pulse. In another aspect, detecting a ventricular complex in the ECG data may be used to identify piezoelectric signal data for use in the pulse detection process, since a characteristic peak in the piezoelectric signal data is expected to occur in time proximity to the occurrence of a ventricular complex if a cardiac pulse is present in the patient. This aspect of the invention is also helpful in identifying whether the patient is in a state of pulseless electrical activity. If a ventricular complex is found in the ECG data and a characteristic peak or other feature indicating a cardiac pulse does not occur in the piezoelectric signal data within an expected time period, the patient may be considered in a state of pulseless electrical activity (PEA) which may be reported to the operator of the device. The operator may also be prompted to deliver PEA-specific therapy to the patient.

Figure 10:
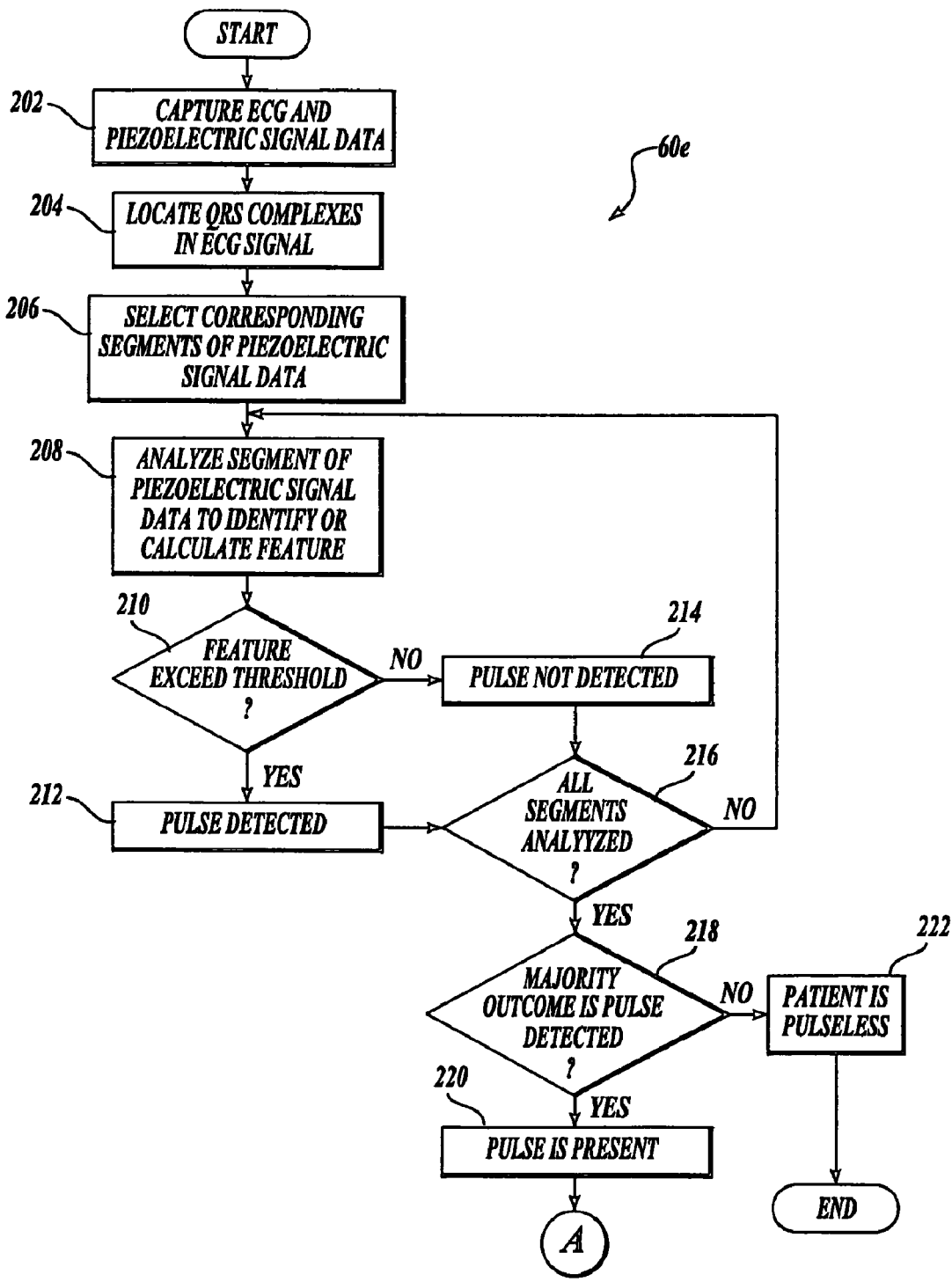
FIG. 10 is a flow diagram of a pulse detection process performed by a defibrillator as shown in FIG. 3 that includes analysis of one or more segments of piezoelectric signal data.

FIG. 10 illustrates another pulse detection process 60*e* that analyzes piezoelectric signal data obtained during time intervals associated with ventricular complexes (e.g., QRS complexes) in the patient's ECG. Beginning in block 202, the pulse detection process 60*e* captures both ECG and piezoelectric signal data, synchronized in time, for a predetermined time interval (e.g., 10 seconds). Alternatively, the ECG and piezoelectric signal capturing step may continue until the first or a specified number of QRS complexes in the ECG have been identified, or in the event of asystole or a low heart rate, a predetermined maximum period of time (e.g., 10 seconds) has passed. During this time, persons around the patient should be advised to not touch the patient (e.g., the device could report "Analyzing now . . . Stand clear").

In block 204, the pulse detection process 60*e* locates QRS complexes in the ECG signal. Identification of QRS complexes can be done using methods published in the literature and well-known to those skilled in the art of ECG signal processing. For example see, Watanabe K., et al., "Computer Analysis of the Exercise ECG: A Review," *Prog Cardiovasc Dis* 22: 423-446, 1980.

In block 206, for each time that a QRS complex was identified in the ECG signal, a segment of piezoelectric signal data obtained from the patient is selected. In one embodiment of the invention, the time window of each segment of piezoelectric signal data is approximately 600 milliseconds in length, and commences in time slightly before the identified QRS complex. If no QRS complexes were identified in the captured ECG signal in block 204 (as would happen for example, during asystole), no segments of piezoelectric signal data are selected in block 206.

In block 208, one or more measurements are made on a segment of piezoelectric signal data selected in block 204 to identify or calculate a feature indicative of a cardiac pulse. Nonlimiting examples of the measurements may include one or more of the following temporal parameters:

(1) peak-to-peak amplitude of the piezoelectric signal data in the segment;

(2) peak-peak amplitude of a derivative of the piezoelectric signal data in the segment;

(3) energy of the piezoelectric signal in the segment (preferably calculated by squaring and summing each of the data values in the segment); or (4) a pattern matching statistic.

The previously-described instantaneous/background energy methods, as well as the spectral methods described herein, could be used in block 208 as well to identify or calculate a feature indicative of a cardiac pulse.

As to pattern matching, the segment of piezoelectric signal data is compared with one or more previously identified piezoelectric signal patterns known to predict the presence of a pulse. The comparison produces a pattern match statistic. Generally, in this context, the greater the value of the pattern match statistic, the closer the patient's piezoelectric signal matches a pattern piezoelectric signal that predicts the presence of a pulse. A measurement resulting from the analysis in block 208 constitutes a feature of the piezoelectric signal data that may be indicative of the presence of a pulse.

In decision block 210, the one or more features from block 208 are evaluated to determine the presence of a cardiac pulse in the patient. The process 60*e* shown in FIG. 10 compares the one or more features to predetermined thresholds to determine whether or not a pulse is detected. For example, a peak-to-peak amplitude measurement would be consistent with the presence of a pulse if the measurement exceeded a predetermined threshold. Similarly, an energy measurement would be consistent with a pulse if its magnitude exceeded a predetermined threshold. Likewise, a pattern matching statistic would be consistent with a pulse if it exceeded a predetermined threshold. If the feature exceeded the specified threshold, the pulse detection process 60*e* determines that a pulse was detected, as indicated at block 212. If the feature did not exceed the specified threshold, a pulse was not detected, as indicated at block 214. If no segments of piezoelectric signal data were selected in block 206 (i.e., no QRS complexes were located in block 202 in the captured ECG), the pulse detection process 60*e* would determine that a pulse was not detected, as indicated at block 214.

While thresholding is used in block 210 to determine whether a pulse was detected, those skilled in the art will recognize other forms of classification that may suitably be used in the invention. For example, a multidimensional classifier may be used in decision block 210 to determine whether a pulse was detected. Separate analyses of the amplitude and energy in the piezoelectric data segment may be performed, with the resultant outcome of each analysis constituting a detection statistic that is provided to the multidimensional classifier. The detection statistics may be weighted and compared in the classifier to determine an overall conclusion whether a pulse is present in the patient. In other embodiments, individual calculations of instantaneous and background amplitudes and/or energies may be provided as detection features for evaluation in a multidimensional classifier. Pattern match statistics may also be evaluated in the multidimensional classifier, as may other measurements of the piezoelectric signal data. Furthermore, spectral techniques can be used, such as the peak frequency or energy techniques described previously. Techniques for constructing multidimensional classifiers are known in the art. See, e.g., R. Duda and P. Hart, *Pattern Classification and Scene Analysis*, referenced earlier and incorporated herein by reference.

After determining whether a pulse was detected (block 212) or not detected (block 214), the pulse detection process 60e determines whether all of the segments of piezoelectric signal data selected in block 206 have been analyzed. If not, the analysis and decision process of blocks 208, 210, 212, and 214 is preferably repeated for a new piezoelectric data segment. This continues until all of the piezoelectric data segments selected in block 206 have been analyzed.

The resulting determination (pulse detected or no pulse detected) may not be the same for each piezoelectric data segment analyzed. An additional decision step is used to determine the overall outcome of the pulse detection process 60e. As indicated at decision block 218, the pulse detection process 60e may evaluate the determinations for each piezoelectric signal data segment and decide that a pulse is present in the patient if a pulse was detected in a simple majority of the segments analyzed. Of course, other voting schemes may be used. If, in decision block 218, a majority is found, the pulse detection process concludes that a cardiac pulse is present in the patient, as indicated at block 220. Otherwise, the pulse detection process 60e concludes that the patient is pulseless, as indicated at block 222.

Requiring a pulse to be found in more than a simple majority of the piezoelectric data segments would improve the specificity of the detection, but decrease the sensitivity for detecting a pulse. Conversely, requiring a pulse to be found for just one piezoelectric data segment or for less than a majority of the piezoelectric segments would improve sensitivity for detecting a pulse but decrease specificity. If the pulse detection process 60e concludes that a pulse is present in the patient, the process 60e may optionally proceed to check the pulse rate of the patient, as illustrated in FIG. 11.

Figure 11:
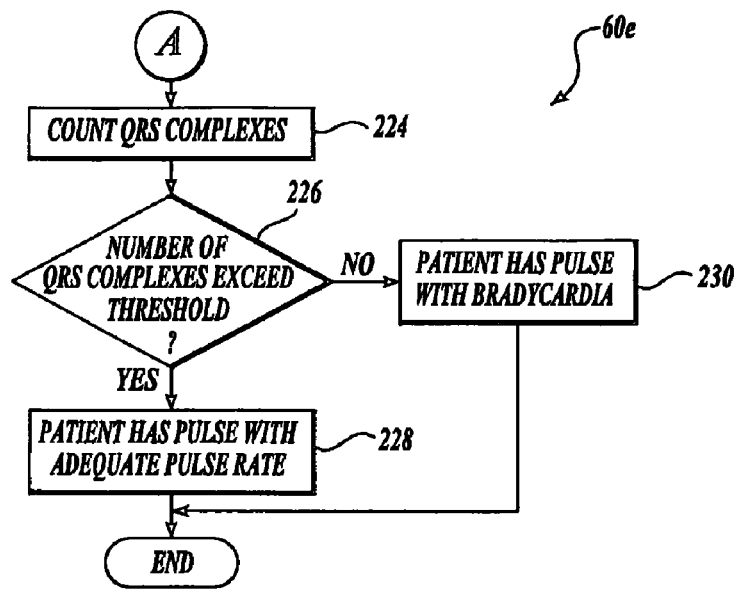
FIG. 11 is a flow diagram of a pulse rate analysis performed with the pulse detection process shown in FIG. 10.

Turning to FIG. 11, in block 224, the number of QRS complexes (located in block 204 in FIG. 10) are counted. Decision block 226 subsequently compares the number of QRS complexes to a threshold. In one exemplary embodiment, the threshold is 5, corresponding to a heart rate of approximately 30 bpm. If the number of QRS complexes is at least equal to the threshold, the pulse detection process 60e proceeds to block 228, concluding that the patient has a pulse and an adequate pulse rate. If the number of QRS complexes is less than the threshold, the pulse detection process 60e proceeds to block 230, concluding that the patient has a pulse, but also severe bradycardia. At very low heart rates, however, the blood flow may be insufficient to support life. For that reason, below a certain heart rate (e.g., 30 bpm), the patient may instead be considered pulseless.

Figure 12:
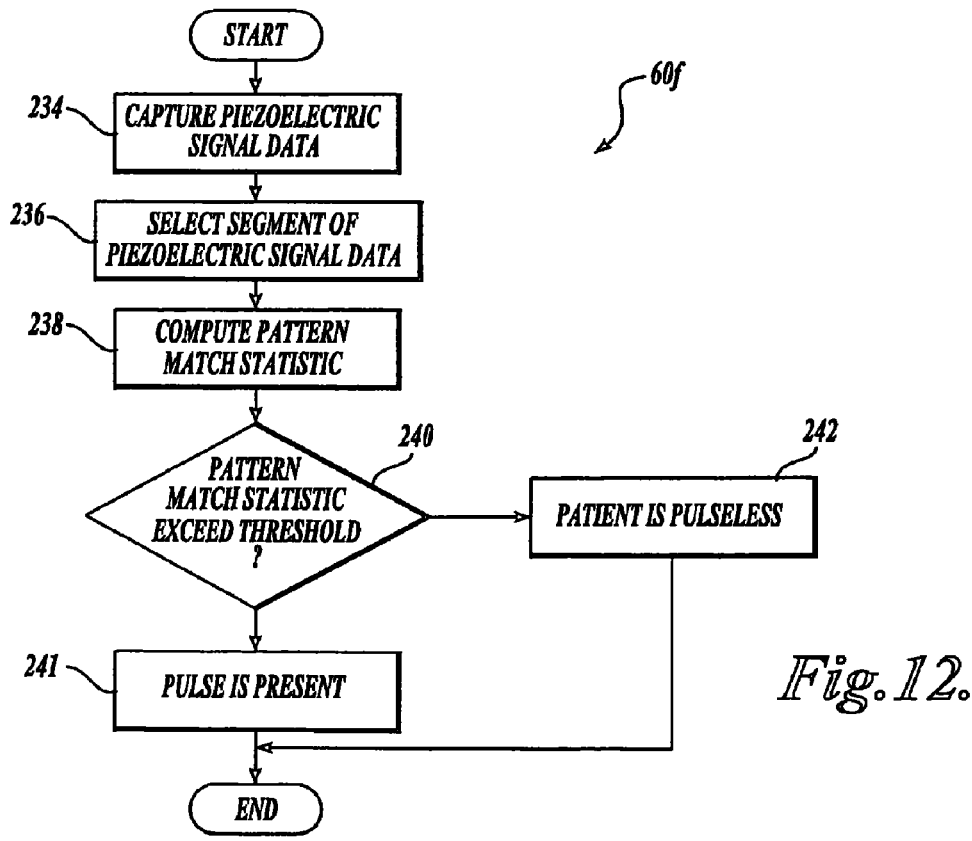
FIG. 12 is a flow diagram of another pulse detection process performed in accordance with the present invention in which a piezoelectric signal pattern analysis is performed.

While the pulse detection process shown in FIG. 10 includes capturing both ECG and piezoelectric signal data, and selecting segments of piezoelectric signal data based on ventricular complexes located in the ECG, other pulse detection processes may not capture or use the ECG signal. In FIG. 12, an alternative pulse detection process 60f begins by capturing only piezoelectric signal data from the patient, as indicated at block 234. Depending on the length of the time interval in which piezoelectric signal data is captured, it may be advantageous to select a segment of the piezoelectric signal data for further analysis, as indicated at block 236. In that regard, one suitable selection process includes scanning the piezoelectric signal data for a peak value and selecting a segment of data that surrounds the detected peak.

For exemplary purposes, the pulse detection process 60f is shown evaluating the selected segment of piezoelectric signal data using a pattern match analysis. However, those skilled in the art will recognize that other techniques (e.g., analysis of the amplitude or energy—temporal or spectral—in the piezoelectric signal data, as discussed above,) may be used. In block 238, the selected piezoelectric data segment is compared with previously identified piezoelectric signal patterns known to predict the presence of a pulse. The resulting pattern match statistic is evaluated against a threshold in decision block 240 to determine whether a pulse was detected in the patient. If the pattern match statistic exceeded the threshold, the pulse detection process 232 concludes in block 241 that a pulse was detected in the patient. Otherwise, the pulse detection process 232 concludes that the patient is pulseless, as indicated in block 242. At this point, the pulse detection process is finished. Alternatively, if a pulse was detected in the patient, the pulse detection process 232 may proceed to evaluate the patient's pulse rate in a manner described in reference to FIG. 11.

The piezoelectric signal obtained from the sensor placed on the patient may include signal elements that are due to cardiac pulse vibrations, respiration, or other patient motion. To assess whether a patient has a pulse, it is desirable to suppress elements in the piezoelectric signal that are due to causes other than cardiac pulses. Signal elements due to non-cardiac causes may contain components at frequencies similar to those due to cardiac pulses. Consequently, bandpass filtering may not always adequately suppress piezoelectric signals due to noncardiac causes.

Signal averaging of the piezoelectric signal can be used to suppress signal elements that are due to noncardiac causes. Signal averaging makes advantageous use of the fact that piezoelectric signal elements due to cardiac pulse vibrations are generally synchronized to ventricular complexes in the ECG signal, whereas other signal elements are generally asynchronous to ventricular complexes. Pulse detection may be more accurately accomplished using an averaged piezoelectric signal.

One preferred method for averaging the piezoelectric signal first stores the continuous ECG and piezoelectric signals, synchronized in time, for a predetermined time interval (e.g., 10 seconds). The timing of the QRS complexes (if any) in the stored ECG signal are determined. Using true mathematical correlation (or an alternative correlation technique such as area of difference), the QRS complexes are classified into types, where all QRS complexes of the same type have high correlation with the first occurring QRS complex of that type. The dominant QRS type is selected as the type containing the most members, with a preference for the narrowest QRS type when a two or more types tie for most members. Using the first QRS of the dominant type as a reference complex, the second QRS complex of the same type is shifted in time until it is best aligned with the reference complex (i.e., it achieves a maximum correlation value). The corresponding piezoelectric signal is also shifted in time to stay synchronized with the time-shifted QRS complex. When the second QRS complex is optimally aligned with the reference complex, the two QRS complexes are averaged together. Segments of the corresponding piezoelectric signals, over a time period from slightly before the start of the QRS complex to about 600 milliseconds after the end of the QRS complex, are also averaged together. The averaged QRS complex is then used as a new reference complex and the process of averaging both the QRS complexes and the corresponding piezoelectric data is repeated with the remaining QRS complexes of the dominant type.

Preferably, during the subsequent averaging of the QRS complexes and piezoelectric data segments, the new QRS complex and piezoelectric segment carry a weight of one and the previous averaged QRS complex and piezoelectric segment carry a weight equal to the number of QRS complexes that have been included in the averaged QRS complex. When all of the QRS complexes of the dominant type have been processed as described above, the averaged piezoelectric signal segment is evaluated using one or more of the techniques previously described (e.g., amplitude, energy, pattern matching), to determine whether the patient has a pulse.

Averaging of piezoelectric signal data may also be accomplished without ECG data. For example, segments of piezoelectric data may be analyzed and classified into types where segments of the same type have a high correlation. Piezoelectric signal data of a dominant type, for example, may then be averaged and evaluated as previously described (using amplitude, energy, pattern matching, etc.) to determine whether the patient has a pulse.

During severe bradycardia, there will be few QRS complexes in a 10-second period and signal averaging of the piezoelectric signal will not be as effective as when the heart rate is higher. However, at very low heart rates, there is unlikely to be enough blood flow to support life. For that reason, below a certain heart rate (e.g., 30 bpm), the patient may be considered pulseless.

Figure 13:
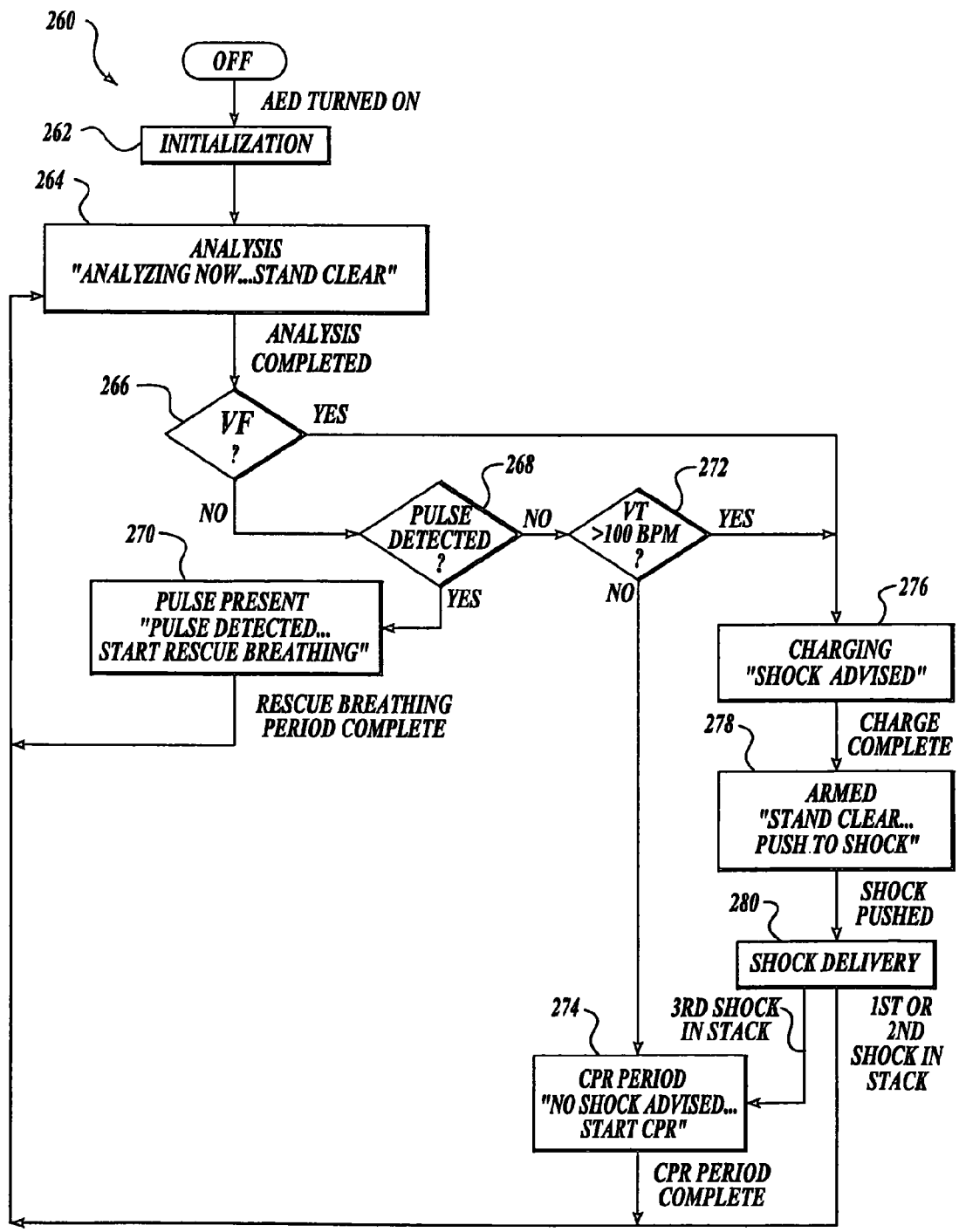
FIG. 13 is a flow diagram of a procedure implemented by a defibrillator as shown in FIG. 3 that incorporates a pulse detection process provided by the present invention.

A pulse detection process as described herein may be used as part of an overall shock advisory process in a defibrillator. The shock advisory process determines whether to recommend defibrillation or other forms of therapy for a patient. FIG. 13 illustrates a pulse detection/defibrillation process 260, preferably for use in an automated external defibrillator (AED) capable of providing a defibrillation pulse if a patient is determined to be pulseless and in ventricular fibrillation or ventricular tachycardia.

In the pulse detection/defibrillation process 260, an AED initializes its circuits when it is first turned on, as indicated at block 262. The defibrillation electrodes of the AED are placed on the patient. When the AED is ready for operation, the process 260 performs an analysis of the patient, as indicated at block 264, in which the AED obtains selected information such as piezoelectric signal data and/or ECG data from the patient. During the analysis performed in block 264, the AED preferably reports "Analyzing now . . . Stand clear" to the operator of the AED.

Using the information obtained in the patient analysis, the process 260 determines in decision block 266 whether the patient is experiencing ventricular fibrillation (VF). If VF is present in the patient, the process 260 proceeds to block 276 where the AED prepares to deliver a defibrillation pulse to the patient. In that regard, an energy storage device within the AED, such as a capacitor, is charged. At the same time, the AED reports "Shock advised" to the operator of the AED.

Once the energy storage device is charged, the process 260 proceeds to block 278 where the AED is ready to deliver the defibrillation pulse. The operator of the AED is advised "Stand clear . . . Push to shock." When the operator of the AED initiates delivery of the defibrillation pulse, the process 260 delivers the defibrillation shock to the patient, as indicated in block 280.

The AED preferably records in memory that it delivered a defibrillation pulse to the patient. If the present pulse delivery is the first or second defibrillation shock delivered to the patient, the process 260 may return to block 264 where the patient undergoes another analysis. On the other hand, if the pulse delivery was the third defibrillation pulse to be delivered to the patient, the process 260 may proceed to block 274 where the AED advises the operator to commence providing CPR therapy to the patient, e.g., by using the message "Start CPR." The "No shock advised" prompt shown in block 274 is suppressed in this instance. The AED may continue to prompt for CPR for a predetermined time period, after which the patient may again be analyzed, as indicated in block 264.

Returning to decision block 266, if VF is not detected in the patient, the process 260 proceeds to decision block 268 and determines whether a cardiac pulse is present in the patient. The pulse detection performed in block 268 may be any one or a combination or variation of the pulse detection processes described above.

Breathing may be checked manually by the operator or automatically by the device, as discussed below in regard to block 374 of FIG. 15. If, at decision block 268, a pulse is detected in the patient and the patient is not breathing, the process 260 proceeds to block 270 and reports "Pulse detected . . . Start rescue breathing" to the operator. The process 260 may also report "Return of spontaneous circulation" if a pulse is detected in the patient any time after the delivery of a defibrillation pulse in block 280. In any event, after a predetermined time period for rescue breathing has completed, the process 260 preferably returns to block 264 to repeat an analysis of the patient.

If a cardiac pulse is not detected at decision block 268, the process 260 determines whether the patient is experiencing ventricular tachycardia (VT) with a heart rate of greater than a certain threshold, e.g., 100 beats per minute (bpm), as indicated at decision block 272. Other thresholds such as 120, 150, or 180 bpm, for example, may be used. If the determination at decision block 272 is negative, the process 260 proceeds to block 274 and advises the operator to provide CPR therapy. Again, at this point, the AED reports "No shock advised . . . Start CPR" to the operator. The prompt to provide CPR is preferably provided for a defined period of time. When the period of time for CPR is finished, the process 260 preferably returns to block 264 and performs another analysis of the patient. If the determination at decision block 272 is positive (i.e., the patient is experiencing VT with a heart rate greater than the threshold), the process 260 performs the shock sequence shown at blocks 276, 278, 280 to deliver a defibrillation pulse.

Figure 14:
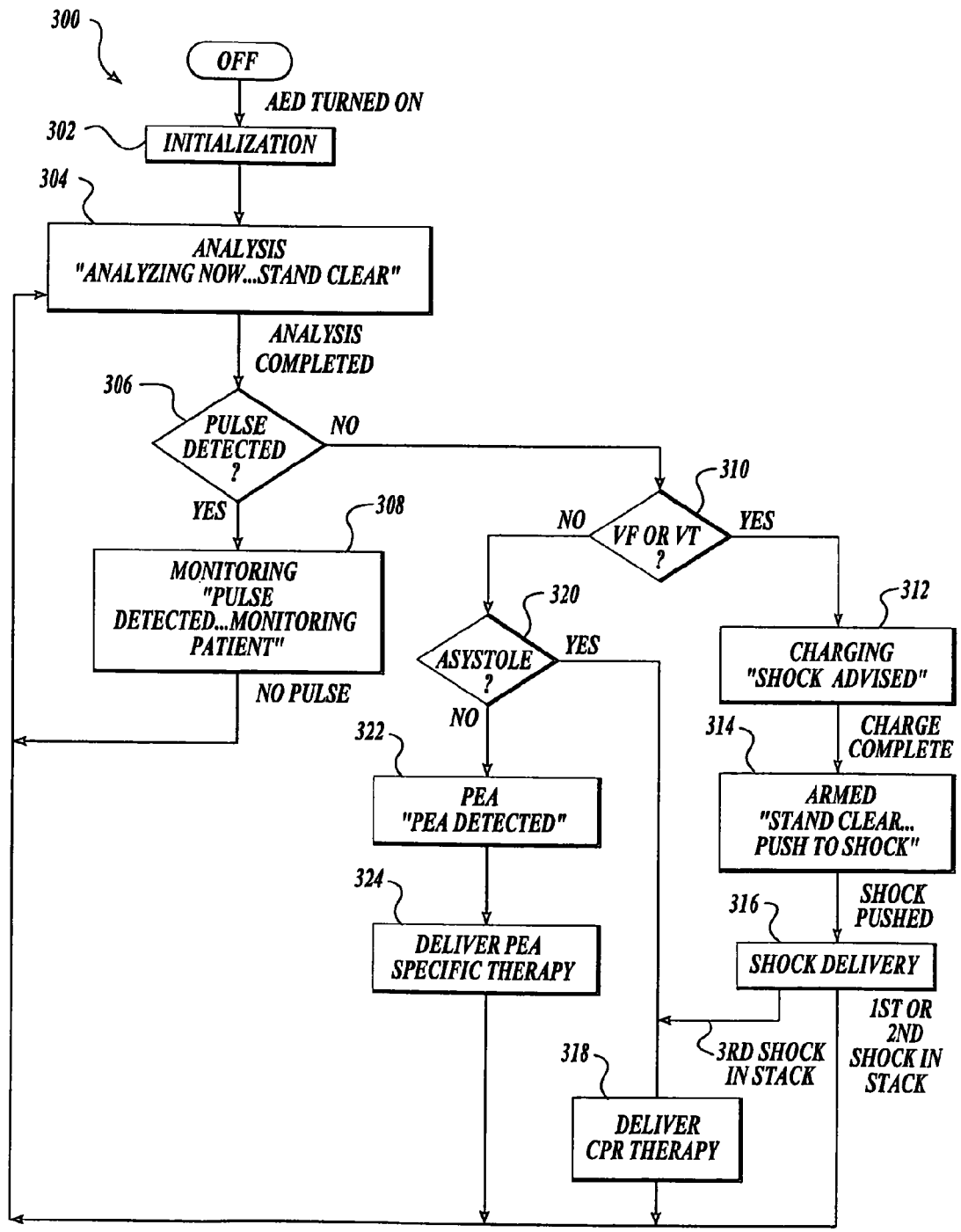
FIG. 14 is a flow diagram of another procedure implemented by a defibrillator as shown in FIG. 3 that incorporates a pulse detection process provided by the present invention.

Those having ordinary skill in defibrillation and cardiac therapy will recognize variations and additions to the process 260 within the scope of the invention. FIG. 14, for example, illustrates an alternative pulse detection/defibrillation process 300 for use in an AED. As with the process 260 in FIG. 15, the AED begins by initializing its circuits at block 302. At block 304, the AED performs an analysis of the patient in a manner similar to that described with respect to block 264 in FIG. 13. After completing the analysis of the patient, the process 300 proceeds to decision block 306 to determine whether a pulse is present in the patient. The pulse detection performed in block 306 may be, for example, any one of the pulse detection processes discussed above or a combination or variation thereof.

If a pulse is detected in the patient, the process 300 may enter a monitoring mode at block 308 in which the patient's pulse is monitored. The pulse monitoring performed at block 308 may use any one or a combination of the pulse detection processes described above. Preferably, the process 300 is configured to proceed from block 308 to block 304 after expiration of the predetermined monitoring time period. If the pulse monitoring at block 308 determines at any time that a pulse is no longer detected, the process 300 returns to block 304 to perform another analysis of the patient. The process 300 also preferably reports the change in patient condition to the operator.

If, at decision block 306, a pulse is not detected in the patient, the process 300 proceeds to decision block 310 where it determines whether the patient has a shockable cardiac rhythm (e.g., VF or VT). As referenced earlier, U.S. Pat. No. 4,610,254, incorporated herein by reference, describes a suitable method for differentiating shockable from non-shockable cardiac rhythms.

If a shockable cardiac rhythm, such as VF or VT, is detected, the process 300 proceeds to a shock delivery sequence at blocks 312, 314, and 316, which may operate in a manner similar to that described with respect to blocks 276, 278, and 280 in FIG. 13. If the pulse delivery was the third defibrillation shock delivered to the patient, the process 300 may proceed to block 318 and prompt the delivery of CPR, as discussed with block 274 in FIG. 13.

If VF or VT is not detected at decision block 310, the process 300 checks for asystole, as indicated at block 320. One suitable process for detecting asystole is described in U.S. Pat. No. 6,304,773, assigned to the assignee of the present invention and incorporated herein by reference. If asystole is detected at block 320, the process 300 proceeds to prompt the delivery of CPR, as indicated at block 318. If asystole is not detected, the process 300 determines that the patient is experiencing pulseless electrical activity (PEA), as indicated at block 322. PEA is generally defined by the presence of ventricular complexes in a patient and the lack of a detectable pulse, combined with no detection of VT or VF. Detection of PEA in block 322 is achieved by ruling out the presence of a pulse (block 306), detecting no VF or VT (block 310), and detecting no asystole (block 320). Alternatively, if the ECG signal is monitored for ventricular complexes (e.g., as shown at block 202 in FIG. 10), the process 300 may conclude the patient is in a state of PEA if it repeatedly observes ventricular complexes without detection of a cardiac pulse associated therewith. If a PEA condition is detected, the process 300 proceeds to block 324 and prompts the operator to deliver PEA-specific therapy to the patient. One suitable method of treating PEA is described in U.S. Pat. No. 6,298,267, incorporated by reference herein. The process 300 may prompt other therapies as well, provided they are designed for a PEA condition. After a PEA-specific therapy has been delivered to the patient, possibly for a predetermined period of time, the process 300 returns to block 304 to repeat the analysis of the patient.

Figure 15:
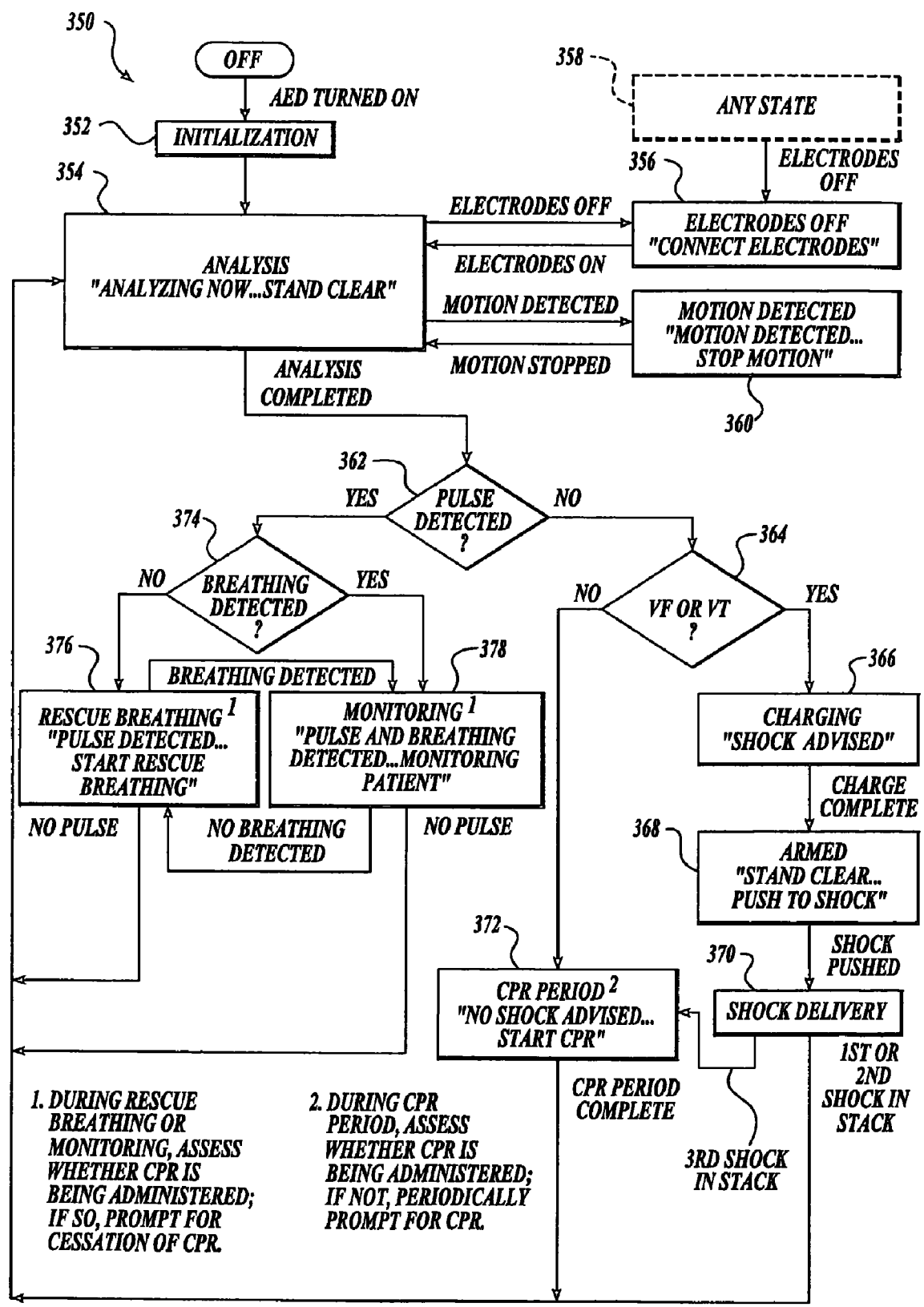
FIG. 15 is a flow diagram of still another procedure implemented by a defibrillator as shown in FIG. 3 that incorporates a pulse detection process provided by the present invention.

FIG. 15 illustrates yet another pulse detection/defibrillation process 350 that may be used in an AED. At block 352, after the AED has been turned on, the AED initializes its circuits. The defibrillation electrodes are also placed on the patient. The AED is then ready to analyze the patient, as indicated at block 354. This analysis may be performed in a manner similar to that described with respect to block 264 in FIG. 13.

If at any point the AED determines that the defibrillation electrodes are not connected to the AED, the process 350 jumps to block 356 where the AED instructs the operator to "Connect electrodes." When the AED senses that the electrodes are connected, the process 350 returns to the analysis in block 354. Likewise, if the AED finds itself in any other state where the electrodes are not connected, as represented by block 358, the process 350 jumps to block 356 where it instructs the operator to connect the electrodes.

Furthermore, during the analysis performed in block 354, if the AED detects motion on the part of the patient, the process 350 proceeds to block 360 where the AED reports to the operator of the AED "Motion detected . . . Stop motion." If the patient is moved during the analysis process 354, the data obtained during the analysis is more likely to be affected by noise and other signal contaminants. Motion of the patient may be detected in an impedance-sensing signal communicated through the patient. A suitable method for detecting motion of the patient is described in U.S. Pat. No. 4,610,254. The AED evaluates the impedance measured between the defibrillation electrodes placed on the patient. Noise and signal components resulting from patient motion cause fluctuations in the impedance signal, generally in a frequency range of 1-3 Hz. If the measured impedance fluctuates outside of a predetermined range, the AED determines that the patient is moving or being moved and directs the process 350 to proceed to block 360. When the motion ceases, the process 350 returns to the analysis in block 354.

The process 350 next proceeds to decision block 362 where it determines whether a pulse is detected in the patient. Again, the pulse detection processes performed in decision block 362 may be, for example, one of the pulse detection processes described above or combination or variation thereof.

If a pulse is not detected in the patient, the process 350 proceeds to decision block 364 where it determines whether the patient has a shockable cardiac rhythm (e.g., VF or VT) or a non-shockable cardiac rhythm (such as asystole and bradycardia). As referenced earlier, one suitable method for differentiating shockable from non-shockable cardiac rhythms is disclosed in U.S. Pat. No. 4,610,254. If the patient's cardiac rhythm is determined to be shockable (e.g., VF or VT is found), the process 350 proceeds to blocks 366, 368, and 370 to deliver a shock to the patient. The shock delivery may be performed as described earlier with respect to blocks 276, 278, 280 in FIG. 13.

If the pulse delivery was the third defibrillation pulse to be delivered to the patient, the process 350 proceeds to block 372 where the AED advises the operator to commence providing CPR therapy to the patient. The CPR prompt may continue for a defined period of time, at which the process 350 returns to block 354 and performs another analysis of the patient.

If, at decision block 364, the patient's cardiac rhythm is determined not shockable, the process 350 preferably proceeds to block 372 and advises the operator to provide CPR therapy, as discussed above.

Returning to decision block 362, if a pulse is detected in the patient, the process 350 proceeds to decision block 374 where it determines whether the patient is breathing. In that regard, the AED may use the impedance signal for determining whether a patient is breathing. Fluctuations in patient impedance below 1 Hz are largely indicative of a change in volume of the patient's lungs. The breathing detection at block 374 (and at blocks 376 and 378, discussed below) may monitor the impedance signal for characteristic changes that indicate patient breathing, e.g., as described in Hoffmans et al., "Respiratory Monitoring With a New Impedance Plethysmograph," *Anesthesia* 41: 1139-42, 1986, which is incorporated by reference herein. Detection of breathing may employ a process that evaluates an amplitude, energy, or pattern in the impedance signal. Preferably, a bandpass filter would be used to isolate the frequency components that more closely demonstrate patient breathing. The piezoelectric signal data may also be analyzed for a component that reveals whether the patient's body is moving due to breathing. If automatic means for detecting breathing in the patient are not available, the AED may ask the operator of the AED to input information (e.g., by pressing a button) to indicate whether the patient is breathing.

If, at decision block 374, the process 350 determines that the patient is not breathing, the process 350 proceeds to a block 376 where the operator of the AED is advised to commence rescue breathing. In that regard, the AED reports to the operator "Pulse detected . . . Start rescue breathing." The AED also continues to monitor the patient's cardiac pulse and returns to block 354 if a cardiac pulse is no longer detected. If, at any point during the provision of rescue breathing, the AED detects that the patient is breathing on his own, the process 350 proceeds to block 378 where the AED monitors the patient for a continued presence of breathing and a cardiac pulse.

Returning to decision block 374, if the process 350 determines that the patient is breathing, the process 350 proceeds to block 378 where the AED monitors the pulse and breathing of the patient. In that regard, the AED reports "Pulse and breathing detected . . . Monitoring patient." If, at any time during the monitoring of the patient the process 350 determines that the patient is not breathing, the process 350 proceeds to block 376 where the operator of the AED is advised to commence rescue breathing. If a cardiac pulse is no longer detected in the patient, the process 350 proceeds from either block 376 or 378 to block 354 to commence a new analysis of the patient.

Lastly, as noted in FIG. 15, during the rescue breathing procedure in block 376 or the monitoring procedure performed in block 378, the AED may assess whether CPR is being administered to the patient. In that regard, signals received from the piezo film sensor 16 shown in FIG. 3 may be used to measure parameters, such as frequency and depth of chest compressions being applied to the patient. If the AED finds that CPR is being performed, the AED may prompt the operator to cease providing CPR. If, during the CPR period of block 372, the AED determines that CPR is not being administered to the patient, the AED may remind the operator to provide CPR therapy to the patient. Another method for determining whether CPR is being administered is to monitor patient impedance to observe patterns of impedance fluctuation in the patient that are indicative of CPR. During CPR, repetitive chest compression typically causes repetitive fluctuations in the impedance signal.

Figure 16:
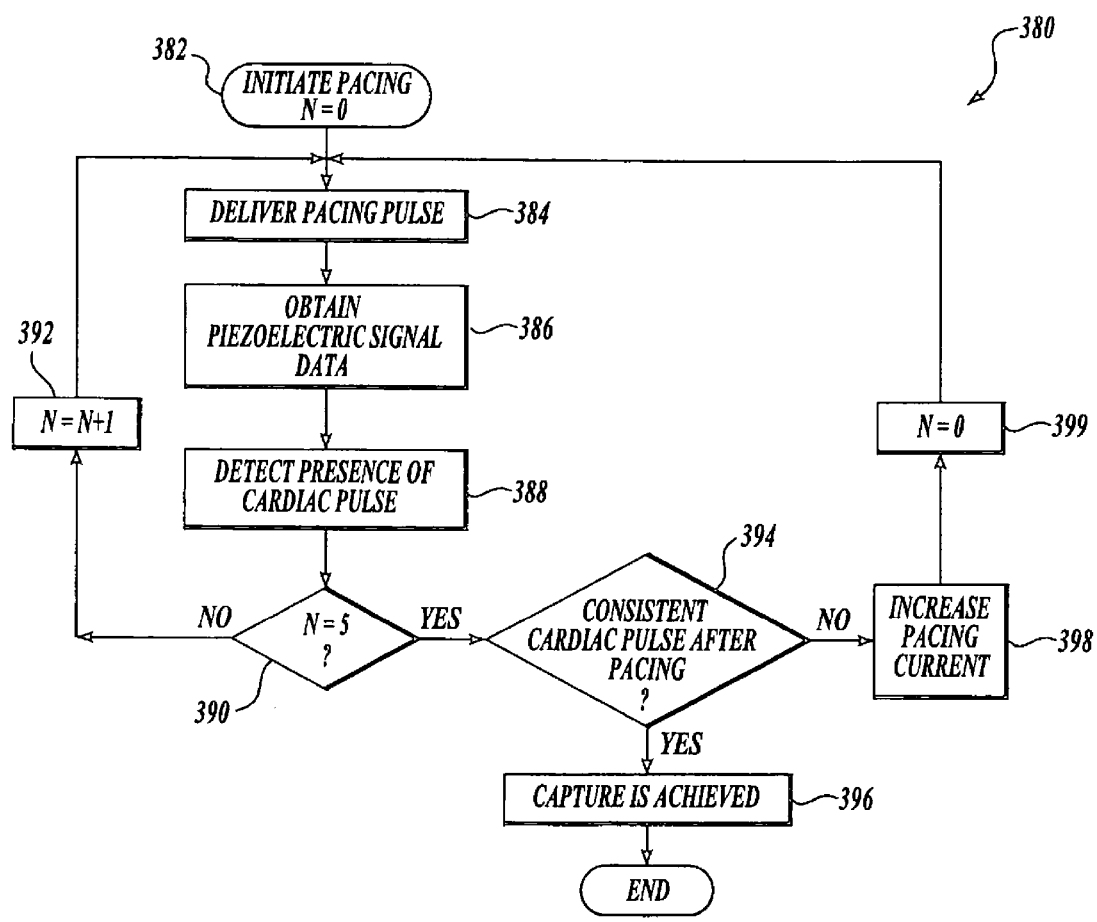
FIG. 16 is a flow diagram of an auto-capture detection process for cardiac pacing that uses a pulse detection process of the present invention.

FIG. 16 illustrates yet another application in which pulse detection according to the present invention may be used. The application described in FIG. 16 pertains to auto-capture detection in cardiac pacing.

Specifically, the auto-capture detection process 380 begins at block 382 in which pacing therapy for the patient is initiated. A counter N, described below, is set to equal 0. At block 384, a pacing pulse is delivered to the patient. Thereafter, piezoelectric signal data is obtained from the patient, as indicated at block 386. The piezoelectric signal data is used in block 388 to detect the presence of a cardiac pulse. The pulse detection process used in block 388 may be, for example, any one or combination or variation of the pulse detection processes discussed above.

The sequence of delivering a pacing pulse and determining the presence of a cardiac pulse in blocks 384, 386, 388 may be repeated a number of times. With respect to FIG. 16, for example, the sequence is repeated five times. At block 390, the counter N is evaluated, and if not yet equal to 5, the counter is incremented by 1 (block 392), following which the process 380 returns to deliver another pacing pulse to the patient (block 384).

If, at decision block 390, the counter N equals 5, the process 380 determines at decision block 394 whether a cardiac pulse occurred consistently after each pacing pulse. The process 380 requires that some portion or all of the pacing pulses result in a detectable cardiac pulse before pronouncing that capture has been achieved. If the presence of a cardiac pulse is determined to consistently follow the pacing pulses, the process 380 determines that capture has been achieved, as in indicated at block 396. Otherwise, the current of the pacing pulses is increased by a predetermined amount, e.g., 10 milliamperes, as indicated at block 398. At block 399, the counter N is set back to equal 0 and the process 380 returns to the pacing capture detection sequence beginning at block 384. In this manner, the pacing current is increased until capture has been achieved.

In FIG. 16, the presence of a pulse is used to determine whether the pacing stimulus has been captured by the ventricles of the patient's heart. Detection of ventricular complexes in the patient's ECG may also be used in connection with piezoelectric signal data to identify pacing capture. For example, a ventricular complex will occur immediately following the pacing stimulus if capture has been achieved. If ventricular complexes are not observed, the current of the pacing pulses may be increased, as discussed above, until capture has been achieved. In an alternative embodiment, a user of the device may be prompted to increase the current of the pacing stimuli prior to the pacing stimuli current being increased.

Figure 17:
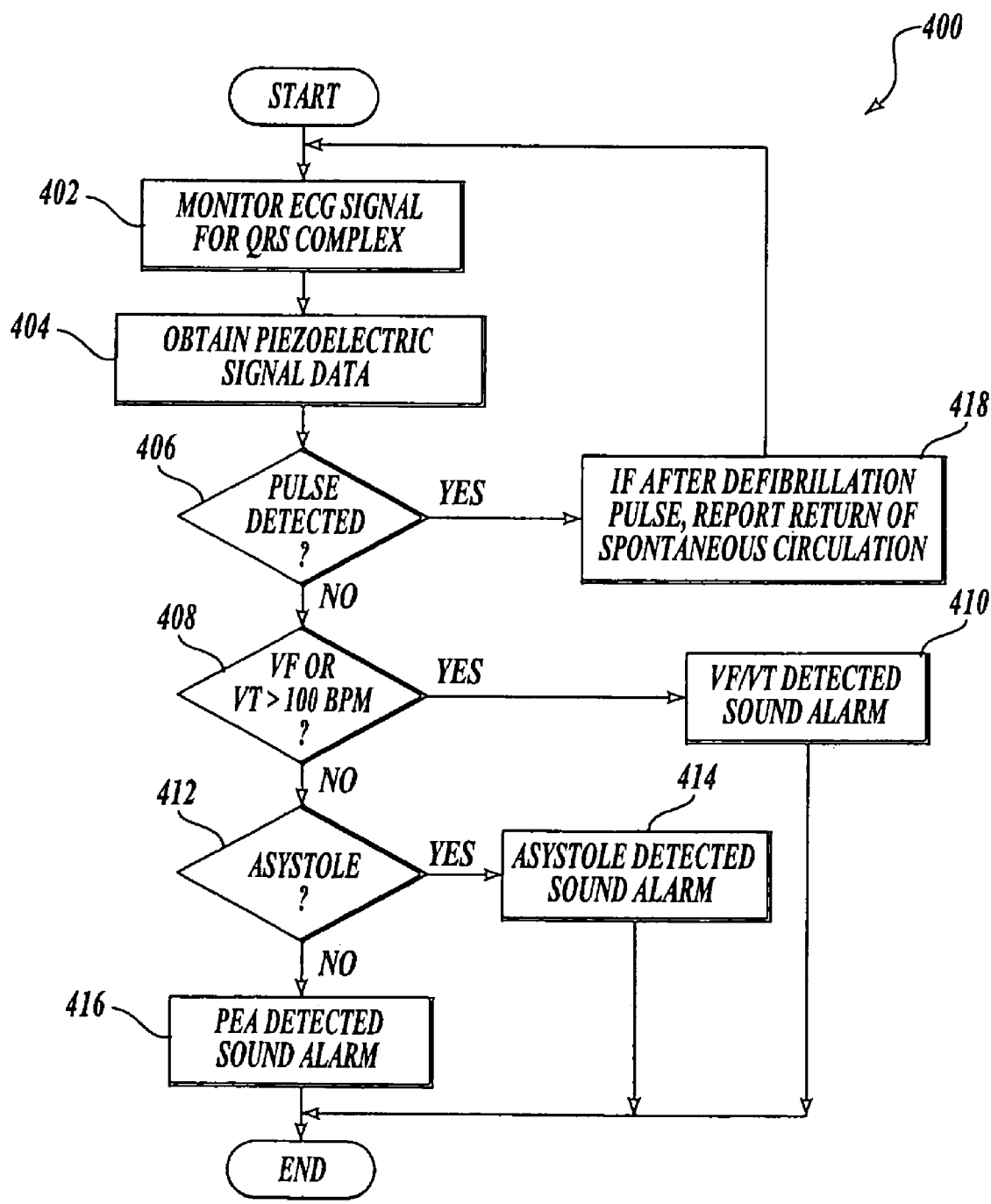
FIG. 17 is a flow diagram of a patient condition advisory process for use in a medical device that incorporates a pulse detection process of the present invention.

FIG. 17 illustrates still another application in which pulse detection according to the present invention may be used. The process 400 described in FIG. 17 is particularly suited for use in a manual defibrillator or patient monitor, though it may be implemented in other forms of medical devices. Beginning at block 402, the process 400 monitors the patient's ECG for QRS complexes. At block 404, the process 400 also obtains piezoelectric signal data from the patient. The process 400 uses the ECG and piezoelectric signal data in decision block 406 to determine the presence of a cardiac pulse. The pulse detection implemented in block 406 may be one or a combination or variation of the pulse detection processes discussed herein.

If a pulse is detected, the process 400 determines whether a defibrillation pulse has been provided to the patient and if so, reports the return of spontaneous circulation to the operator, as indicated at block 418. The process 400 then returns to block 402 to repeat the pulse detection analysis. If a pulse is not detected, the process 400 evaluates the ECG signal to determine whether the patient is experiencing ventricular fibrillation or ventricular tachycardia with a heart rate greater than 100 bpm. If so, then the process identifies the patient's condition and produces a VT/VF alarm, as indicated at block 410. If not, the process 400 then proceeds to block 412 to check for an asystole condition.

Detection of asystole may be accomplished as noted earlier and described in U.S. Pat. No. 6,304,773, incorporated herein by reference. If asystole is detected, the process 400 identifies the patient's condition and sounds an asystole alarm, as indicated at block 414. Otherwise, the patient is experiencing PEA and the patient's condition is so identified, with the sound of a PEA alarm, as indicated at block 416. In this manner, the operator of the manual defibrillator or monitor is kept advised of the patient's condition.

While various exemplary embodiments of the invention have been illustrated and described herein, persons having ordinary skill in the art will recognize variations of the same that are fully with the scope of the invention. Embodiments of the invention described herein are shown processing digital piezoelectric signal data. However, the invention also includes embodiments in which the piezoelectric signal data is not converted to digital form, but remains in analog form. References to "data" thus encompass both digital and analog signal formats. Moreover, references to "piezoelectric signal data" may refer to the raw piezoelectric signal itself or signal information derived from the piezoelectric signal in either digital or analog form.

The embodiments of the invention in which an exclusive property or privilege is claimed are defined as follows:

1. A medical device for detecting presence of a cardiac pulse, comprising:
   a piezoelectric sensor having a transducing element configured for placement on a surface of a patient's body, the transducing element being adapted to sense movement in the patient's body due to the cardiac pulse and produce piezoelectric signal data in response thereto;

processing circuitry configured to analyze the piezoelectric signal data for a feature indicative of the presence of the cardiac pulse and determine whether the cardiac pulse is present based on the feature; and an electrotherapy generator for delivering pacing stimuli to the patient, wherein the processing circuitry analyzes the piezoelectric signal data to determine whether the cardiac pulse occurred in the patient in response to delivery of a pacing stimulus of the pacing stimuli, to the patient.

2. The medical device of claim 1, in which the processing circuitry is configured to increase a current of further pacing stimuli to be delivered to the patient if the cardiac pulse did not occur in the patient in response to the delivery of the pacing stimulus.

3. The medical device of claim 1, wherein the processing circuitry is configured to prompt a user of the device to increase a current of further pacing stimuli to be delivered to the patient based on the determination.

* * * * *